US012758375B2

(12) United States Patent
Zhen et al.

(10) Patent No.: US 12,758,375 B2
(45) Date of Patent: Oct. 13, 2026

(54) HOLDER, PACKAGING BOX, AND PACKAGING SYSTEM FOR PROSTHETIC VALVE

(71) Applicant: VENUS MEDTECH (HANGZHOU) INC., Hangzhou (CN)

(72) Inventors: Ni Zhen, Hangzhou (CN); Yuehong Zhang, Hangzhou (CN); Jian Wang, Hangzhou (CN); Xiang Wang, Hangzhou (CN); Qun Dong, Hangzhou (CN); Yuxuan Du, Hangzhou (CN)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 106 days.

(21) Appl. No.: 18/677,926

(22) Filed: May 30, 2024

(65) Prior Publication Data

US 2024/0307165 A1 Sep. 19, 2024

Related U.S. Application Data

(63) Continuation of application No. PCT/CN2022/130360, filed on Nov. 7, 2022.

(30) Foreign Application Priority Data

Dec. 30, 2021 (CN) ......................... 202111650026.7
Dec. 30, 2021 (CN) ......................... 202123449496.5

(51) Int. Cl.
*A61F 2/00* (2006.01)
*A61F 2/24* (2006.01)

(52) U.S. Cl.
CPC .......... *A61F 2/0095* (2013.01); *A61F 2/2412* (2013.01)

(58) Field of Classification Search
CPC ...... A61F 2/0095; A61F 2/2412; A61F 2/013; A61F 2/02; A61F 2/24; A61F 2/2418; B65D 81/02; B65D 85/00
(Continued)

(56) References Cited

U.S. PATENT DOCUMENTS 4,801,015 A 1/1989 Lubock et al.
5,236,450 A 8/1993 Scott
(Continued)

FOREIGN PATENT DOCUMENTS

CN 2635574 Y 8/2004
CN 105705116 A 6/2016
(Continued)

OTHER PUBLICATIONS

International Search Report and Written Opinion for corresponding PCT Application No. PCT/CN2022/130360.
(Continued)

*Primary Examiner* — Rafael A Ortiz

(57) ABSTRACT

A holder for a prosthetic valve includes a base, claw locks and a holding handle. The base has opposite bottom and top sides. The prosthetic valve assembly area is defined on the bottom side. The claw locks are connected to the base and located on the bottom side of the base. The claw locks are arranged around the prosthetic valve assembly area. The holding handle is connected to the base and is located on the top side of the base. In this solution, the claw locks are in a clearance fit with the connecting ears or mesh gaps to facilitate the connection or disconnection between the holder and the prosthetic valve.

14 Claims, 22 Drawing Sheets

(58) Field of Classification Search
USPC .......................................................... 206/438
See application file for complete search history.

(56) References Cited

U.S. PATENT DOCUMENTS

| | | | | |
|---|---|---|---|---|
| 5,720,391 | A | 2/1998 | Dohm et al. | |
| 10,188,516 | B2 * | 1/2019 | Tuval .................... | A61F 2/2418 |
| 2013/0289699 | A1 * | 10/2013 | Green ................... | A61F 2/2412 623/1.11 |
| 2014/0039609 | A1 * | 2/2014 | Campbell ............. | A61F 2/2412 623/2.11 |
| 2014/0107767 | A1 * | 4/2014 | Braido ................... | A61B 50/30 623/2.11 |
| 2014/0230515 | A1 | 8/2014 | Tuval et al. | |

FOREIGN PATENT DOCUMENTS

| | | | | |
|---|---|---|---|---|
| CN | 217295237 | U | 8/2022 | |
| EP | 2921135 | A1 * | 9/2015 | ........... A61F 2/2427 |
| WO | 2014/022300 | A1 | 2/2014 | |
| WO | WO-2016046599 | A1 * | 3/2016 | ........... A61F 2/0095 |
| WO | 2019/212812 | A1 | 11/2019 | |
| WO | 2019/224580 | A1 | 11/2019 | |

OTHER PUBLICATIONS

Partial European Search Report Issued on Dec. 10, 2025 for Corresponding European Application No. 22913809.4.

* cited by examiner

HOLDER, PACKAGING BOX, AND PACKAGING SYSTEM FOR PROSTHETIC VALVE

CROSS-REFERENCE TO RELATED APPLICATIONS

The present disclosure is a Continuation Application of PCT Application No. PCT/CN2022/130360, filed on Nov. 7, 2022, which claims the priorities of Chinese Patent Application No. 202111650026.7, filed on Dec. 30, 2021, and Chinese Patent Application No. 202123449496.5, filed on Dec. 30, 2021, the entire contents of which are hereby incorporated by reference.

TECHNICAL FIELD

The present disclosure relates to the field of medical device, and in particular to a holder, a packaging box and a packaging system for a prosthetic valve.

DESCRIPTION OF THE PRIOR ART

A prosthetic valve is mainly used to replace a diseased valve, including a cylindrical stent and leaflets connected to the stent. The stent can generally be formed by cutting or weaving. In order to achieve radial deformability, most stents have a mesh structure. Connecting ears adapted to the delivery system can be provided at one axial end of the stent as needed.

Prosthetic valves are divided into dry films (also called dry valves) and wet films, depending on the storage method. When the dry film is stored in a container, a holder is used to engage with the connecting ears or the mesh gaps for positioning the dry film. However, the connection and disconnection of the existing holders with the prosthetic valves are relatively complicated.

SUMMARY OF THE DISCLOSURE

In order to solve the above technical problems, the present disclosure discloses a holder for a prosthetic valve, including:

- a base having a bottom side and a top side opposite to each other, wherein a prosthetic valve assembly area is defined on the bottom side;
- a plurality of locks connected to the base, wherein the locks are distributed around the prosthetic valve assembly area, and the locks are configured to engage with the prosthetic valve; and
- a driving part linked with the locks and having a first position and a relative second position relative to the base, wherein in the first position, the locks hold the prosthetic valve in the prosthetic valve assembly area, and in the second position, the locks are disengaged from the prosthetic valve and allow the prosthetic valve to move out of the prosthetic valve assembly area.

In the following, several alternatives are provided, but merely as further additions or preferences, instead of as additional limitations to the above-mentioned technical solution. Without technical or logical contradiction, the alternatives can be combined with the above-mentioned technical solution, individually or in combination.

Optionally, the driving part is fixedly connected to the base, and is configured to switch between the first position and the second position by deformation of the driving part itself and/or the base.

Optionally, the driving part is movably connected to the base, and is configured to switch between the first position and the second position through movement relative to the base.

Optionally, the base is formed by separate pieces, the driving part is connected to the separate pieces of the base and is configured to switch between the first position and the second position by combining and splitting the separate pieces of the base.

Optionally, the holder for the prosthetic valve further includes a holding handle, and the holding handle is connected to the base and is located on the top side of the base.

Optionally, the driving part also serves as the holding handle, or the driving part and the holding handle are separately configured and connected to the base respectively.

Optionally, the locks and the prosthetic valve are engaged with each other in at least one of the following configurations:

- the prosthetic valve has a cylindrical structure as a whole and a side wall with structural gaps, and the locks extend into the structural gaps when engaging with the prosthetic valve;
- the prosthetic valve is provided with connecting ears, and the locks grip the connecting ears when engaging with the prosthetic valve.

Optionally, the locks are claws, at least a part of the base is a connecting portion, at least one of the claws is a movable claw connected to a bottom side of the connecting portion, the driving part is a driving handle provided on a top side of the connecting portion, and the driving handle is linked with the movable claw through the connecting portion.

Optionally, a portion of the base adjacent to the connecting portion is a deformable portion, and the deformable portion is made of a resilient material.

The movable claw has an initial state in which the prosthetic valve is gripped and a relative unlocked state in which the prosthetic valve is released; the driving handle is linked with and configured to drive the movable claw to move toward the unlocked state, and the movable claw is configured to reset to the initial state through the deformable portion.

Optionally, the base has a radial direction in space, and each claw includes a connecting arm fixed to the base and a claw head located on the connecting arm and protruding in the radial direction, wherein the claw head is configured to engage with the prosthetic valve.

Optionally, the base is further connected to supporting arms arranged in pair, and in the circumferential direction of the base, the supporting arms in the same pair are located on two sides of the movable claw respectively.

Optionally, the holder for the prosthetic valve further includes a holding handle, and the holding handle is connected to the base and is located on the top side of the base.

Optionally, the holding handle is located in a central area of the base.

Optionally, the base has a frame structure, including:

- an outer ring, wherein the claws are arranged at intervals on the outer ring; and
- transition arms extending from an inner edge to a central area of the outer ring and connected to the driving part.

Optionally, the deformable portion is a section of the outer ring.

Optionally, a section of the outer ring is axially narrowed or radially narrowed to form the deformable portion.

Optionally, the transition arms have a radiating distribution.

Optionally, the base has a frame structure and includes:
a middle part;
transition arms, which extend from the middle part outwardly in a radial pattern; and
connecting portions located at ends of the transition arms extending outwardly in the radial pattern.

Optionally, the transition arms are divided into a plurality of groups, the driving part includes a plurality of driving handles which are connected to the corresponding transition arms in the corresponding groups.

Optionally, the base has a radial direction in space, and each claw includes a connecting arm fixed to a corresponding connecting portion and a claw head located on the connecting arm and protruding in the radial direction, wherein the claw head is configured to engage with the prosthetic valve.

Optionally, relative to the connecting portions, the driving handle is located on the top side of the base, and the locks are located on the bottom side of the base.

Optionally, there are two transition arms in a same group, each driving handle is in a first arc shape and two ends thereof are respectively connected to ends of corresponding transition arms, and the connecting arm is in a second arc shape and two ends thereof are respectively connected to the ends of the corresponding transition arms.

The first arc is located on a first reference plane, the second arc is located on a second reference plane, and an angle α between the first reference plane and the second reference plane is at least 30 degrees.

Optionally, in the first position, all connecting arms are coplanar and surround the prosthetic valve assembly area, and tops of the driving handles are away from each other.

In the second position, the tops of the driving handles are close to each other to drive the connecting arms away from the prosthetic valve assembly area.

Optionally, the base defines an installation through-hole, two pillar-shaped driving parts are provided and pass through the installation through-hole respectively, the locks are claws, and the claws are fixed to the corresponding driving parts.

A resilient element is provided between the two driving parts to adapt to a relative movement of the two driving parts and to drive the two driving parts to reset.

Optionally, the installation through-hole is elongate, in the first position, the two driving parts are respectively located at two ends of the installation through-hole under an action of the resilient element, and in the second position, the two driving parts approach each other or tilt to cause the claws to release the prosthetic valve.

Optionally, a block is provided on the bottom side of the base, and in the initial state, the claws are close to the inner side of the block.

Optionally, two driving parts are slidably fitted in the installation through-hole in the length direction of the installation through-hole.

Optionally, each driving part has a first positioning portion located on the top side of the base and a second positioning portion located on the bottom side of the base, and the first positioning portion and the second positioning portion cooperate with each other to limit a movement path of a corresponding driving part.

Optionally, the first positioning portion is a limiting tooth, and the second positioning portion is a limiting tooth or a step structure at a portion connected with the corresponding claw.

Optionally, the claws and the corresponding driving part are formed in a single piece.

Optionally, the claw includes:
a connecting arm fixed to a portion of a corresponding driving part on the bottom side of the base;
a claw head located on the connecting arm and protruding radially for engaging with the prosthetic valve.

Optionally, the resilient element has a deformable frame structure.

Optionally, there are two claws on the same driving part, and they are respectively located on two opposite sides of the driving part.

Optionally, the locks are claws, the base is formed by separate pieces and includes a plurality of base units that fit with each other, and the claws are distributed on the base units.

Optionally, the base is disc-shaped, and the base units fit with each other in a radial direction of the base.

Optionally, the base units are movably inserted one in the other.

Optionally, the driving part includes a plurality of handle units that are fitted with each other, each handle unit is connected to a corresponding base unit, and the driving part also serves as a holding handle.

Optionally, there are two base units, each including:
an outer ring, which has an insertion fitting at a circumferential end thereof for engaging with the other base unit; and
a transition arm extending from an inner edge to a central area of the outer ring and connected to a corresponding handle unit.

Optionally, each claw includes a connecting arm and a claw head located on the connecting arm and protruding radially for engaging with the prosthetic valve.

On the same base unit, connecting arms of all claws are fixed to the outer ring or the transition arm.

Optionally, the quantity of the claws on the same base unit is 2, 3 or 4, depending on the quantity of the claw heads, and the connecting arms of all the claws are connected into one piece.

Optionally, on the same base unit, the connecting arms of all the claws are connected into an arc-shaped rib, and the arc-shaped rib is fixed to the transition arm.

Optionally, the base defines engagement openings for the prosthetic valve to pass through.

The locks are movably mounted on the base, and relative to the base, the locks have an initial state in which the locks restrict the prosthetic valve passing through the engagement openings, and an unlocked state in which the prosthetic valve passing through the engagement openings is allowed to disengage from the engagement openings.

The driving part is movably mounted on the base and is linked with the locks to drive the locks to move toward the unlocked state.

Optionally, the base is plate-shaped and has top and bottom sides opposite to each other in a thickness direction thereof, wherein the prosthetic valve assembly area is defined on the bottom side, and the locks are located on the top side of the base.

The top side of the base is fixedly provided with lock seats adjacent to the corresponding engagement openings, and the locks are inserted into the corresponding lock seats in the initial state.

Optionally, each lock is rod-shaped and has a length sufficient to span across a corresponding engagement opening, and a corresponding lock seat defines an insertion hole for accommodating the lock.

Optionally, each lock seat spans across a corresponding engagement opening, and in the initial state, two ends of a corresponding lock are overlapped on two opposite sides of the corresponding engagement opening.

Optionally, the base defines a guide groove, the driving part is slidably engaged in the guide groove, and the holder further includes a transmission arm located on the top side of the base and connected between the driving part and the locks.

Optionally, the driving part includes a root engaged with the guide groove and a handle extending from the root toward the top side of the base, two opposite sides of the root define clamping grooves, and groove walls of the guide grooves are engaged with the clamping grooves on corresponding sides.

Optionally, one end of the guide groove points to a middle area of the base, and the other end extends to and opens to an edge of the base.

Optionally, the transmission arm is belt-shaped in a form of a deformable quadrilateral, and two driving parts are arranged at diagonal positions of the quadrilateral, and two locks are arranged at the other diagonal positions of the quadrilateral.

The transmission arm is made of a resilient material and configured to drive the two locks to move toward the initial state, and when the two driving parts approach each other, the two locks are driven through the transmission arm to move toward the unlocked state.

The present disclosure further provides a packaging box for a prosthetic valve, including an outer box, wherein the outer box includes an outer box body and a box cover that match with each other, and the holder described in the present disclosure is placed in the outer box body.

Optionally, a positioning step is provided on an inner wall of the outer box body, and the bottom side of the base rests on the positioning step.

Optionally, an anti-detachment protrusion is further provided on the inner wall of the outer box body, and the anti-detachment protrusion is located on the top side of the base and limits an edge of the base.

Optionally, in a height direction of the outer box body, top and bottom of the anti-detachment protrusion are each provided with an inclined guide surface.

Optionally, at least a portion of an edge of the base is concave, and a gap is defined between an edge of the concave portion and an inner wall of the outer box body and is communicated to a space below the base.

Optionally, a cross-section of the outer box body is in shaped of a rectangle, and the concave portion is located at a corner of the rectangle.

The present disclosure further provides a packaging box for a prosthetic valve, which includes an inner container and an outer box in a nested configuration. The inner container is provided with a holder described in the present disclosure, and the opening of the inner container is covered with a first sealing film.

The outer box includes an outer box body and a box cover which are snapped with each other, the inner container is located in the outer box body, and an opening of the outer box body is covered with a second sealing film.

Optionally, a circumferential positioning mechanism is provided between an inner wall of the outer box body and an outer wall of the inner container.

Optionally, the circumferential positioning mechanism includes:

- a positioning groove, opened in one of the inner wall of the outer box body and the outer wall of the inner container; and
- a positioning rib, located on the other of the inner wall of the outer box body and the outer wall of the inner container and engaging with the positioning groove.

Optionally, the outer peripheral wall of the box cover is provided with a force application portion protruding outwardly.

Optionally, a middle box is further provided between the outer box and the inner container, the middle box includes a middle box body and a third sealing film covering an opening of the middle box body, and the inner container is located in the middle box body.

Optionally, the first sealing film is made of a breathable and waterproof material.

The third sealing film is made of a breathable and waterproof material.

The second sealing film is made of a non-breathable and waterproof material.

Optionally, a circumferential positioning mechanism is provided between an inner wall of the middle box body and an outer wall of the inner container.

Optionally, a spacer is provided between the middle box body and the outer box body to create a gap between them.

Optionally, the gap between the middle box body and the outer box body includes a radial gap and/or a bottom gap.

Optionally, the spacer is a protrusion which is a part of one of the middle box body and the outer box body and abuts against the other of the middle box body and the outer box body.

Optionally, the outer box body has a double-layer structure, including:

- an outer layer, an inner wall of which defines a slot; and
- an inner layer, a top of which has an opening and has a top plate extending outwardly at the opening, wherein an edge of the top plate has a snap engaging with the slot, and the second sealing film is attached and fixed to the top plate.

Optionally, a temperature sensor is provided inside the double-layer structure, a temperature display screen is embedded in a side wall of the outer layer, and the temperature display screen is configured to receive signals from the temperature sensor and display the same accordingly.

Optionally, the inner wall of the outer layer is fitted and fixed with a lining plate, and the slot is opened on the lining plate on a corresponding side.

Optionally, one side of the top plate extends and forms a storage bin with a top opening, and an outer wall of the storage bin and the corresponding outer side of the outer layer define an access opening communicated to the opening of the storage bin.

Optionally, a middle part of the top plate has a sunken area, the inner layer is cylindrical with the opening thereof located in the sunken area, the opening of the middle box body has an outer flange, and the outer flange is overlapped on a top surface of the sunken area.

The present disclosure further provides a packaging box for a prosthetic valve, which includes an inner container and an outer box in a nested configuration. The inner container is provided with a holder described in the present disclosure, and the outer box is in the shape of a soft bag.

The present disclosure further provides a packaging system for a prosthetic valve, including:

- a packaging box including an outer box, a middle box and an inner container arranged in sequence from outside to inside;
- a holder located in the inner container and provided with locks;

a prosthetic valve located in the inner container, which is cylindrical and has hollow structural gaps on a side wall thereof, wherein the locks extend into corresponding structural gaps.

The packaging box and the holder in the packaging system for the prosthetic valve can be the packaging box and the holder described above in the present disclosure.

Optionally, the prosthetic valve is suspended in the inner container.

Optionally, the prosthetic valve is a dry valve.

Optionally, in the radial direction of the prosthetic valve, the locks are located inside or outside the prosthetic valve, and are in a transition fit with the prosthetic valve in the radial direction.

Optionally, the outer box is in the shape of a soft bag.

The specific benefits will be further explained in the specific embodiments referring to the specific structures or steps.

LIST OF REFERENCE SIGNS

Figure 1:
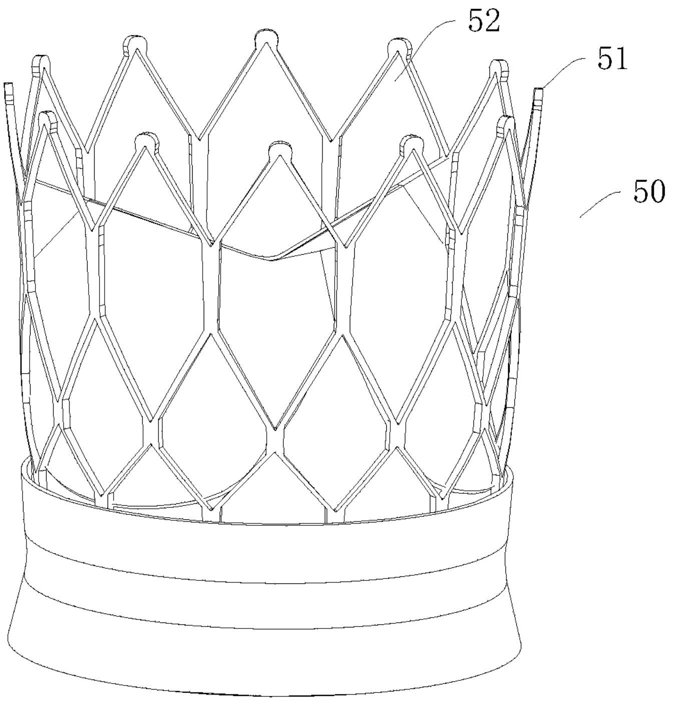
FIG. 1 is a schematic view of a prosthetic valve according to an embodiment of the present disclosure.

10, packaging box; 101, packaging box; 102, packaging box; 103, packaging box; 11, outer box; 111, outer box body; 112, box cover; 113, second sealing film; 114, force application portion; 115, sealing ring; 12, inner container; 121, first sealing film; 122, limiting step; 123, attachment portion; 13, positioning mechanism; 131, positioning groove; 132, positioning rib; 133, flared section; 14, sleeve;

20, holder; 21, base; 211, outer ring; 212, transition arm; 2121, connecting rod; 213, connecting portion; 2131, deformable portion; 214, driving handle; 215, supporting arm; 216, bottom side; 217, top side; 218, prosthetic valve assembly area; 22, claw; 221, movable claw; 222, connecting arm; 223, claw head; 23, holding handle;

30, holder; 31, base; 311, installation through-hole; 312, bottom side; 313, top side; 314, prosthetic valve assembly area; 315, flange; 316, block; 32, claw; 321, connecting arm; 322, claw head; 33, driving part; 331, resilient element; 332, limiting tooth; 333, step structure;

40, holder; 41, base; 411, base unit; 412, outer ring; 4121, slot; 4122, insertion block; 413, transition arm; 414, bottom side; 415, top side; 416, prosthetic valve assembly area; 42, claw; 421, claw head; 422, arc-shaped rib; 43, driving part; 431, handle unit;

50, prosthetic valve; 51, stent; 52, mesh gap;

60, holder; 61, base; 611, connecting portion; 612, bottom side; 613, top side; 614, prosthetic valve assembly area; 615, transition arm; 62, lock; 621, connecting arm; 622, claw head; 63, middle part; 64, driving handle;

70, packaging box; 701, packaging box; 702, packaging box; 703, packaging box; 71, outer box; 711, outer box body; 7111, access opening; 712, box cover; 713, second sealing film; 714, outer layer; 7141, slot; 7142, lining plate; 715, inner layer; 7151, top plate; 7152, snap; 7153, sunken area; 716, storage bin; 72, middle box; 721, third sealing film; 722, middle box body; 7221, outer flange; 73, spacer; 74, temperature sensor; 75, circumferential positioning mechanism; 751, positioning groove; 752, positioning ribs,

80, holder; 81, base; 811, top side; 812, bottom side; 813, prosthetic valve assembly area; 814, engagement opening; 815, guide groove; 816, flared section; 817, concave portion; 82, lock; 821, planar surface; 822, arc surface; 83, driving part; 831, root; 8311, first limiting portion; 8312, second limiting portion; 8313, connecting portion; 832, handle; 833, clamping groove; 84, lock seat; 85, insertion hole; 86, transmission arm; 861, arm unit;

90, packaging box; 91, outer box; 911, outer box body; 9111, step unit; 913, guide surface; 912, box cover; 914, positioning step; 915, anti-detachment protrusion.

DESCRIPTION OF EMBODIMENTS

The technical solutions according to the embodiments of the present disclosure will be described clearly and fully in combination with the drawings according to the embodiments of the present disclosure. Obviously, the described embodiments are not all embodiments of the present disclosure, but only part of the embodiments of the present disclosure. Based on the disclosed embodiments, all other embodiments obtained by those skilled in the art without creative work fall into the scope of this invention.

It should be noted that, when a component is "connected" with another component, it may be directly connected to another component or may be indirectly connected to another component through a further component. When a component is "provided" on another component, it may be directly provided on another component or may be provided on another component through a further component.

Unless otherwise defined, all technical and scientific terms used herein have the same meaning as commonly understood by a person skilled in the art. The terms in the description of the present disclosure are used to describe specific embodiments, and not to limit the present disclosure. The term "and/or" used herein includes one or more of the listed options in any combinations, or the combination of all of the listed options.

The present disclosure discloses a holder, including a base, locks, and a driving part. The base has a bottom side and a top side opposite to each other. The prosthetic valve assembly area is defined on the bottom side for assembling a prosthetic valve 50. The driving part is used to drive the locks to release the connection with the prosthetic valve 50.

Taking the prosthetic valve 50 in FIG. 1 as an example, the prosthetic valve generally has a cylindrical structure and has structural gaps on the side wall thereof. For example, the prosthetic valve 50 includes a stent 51 and leaflets connected in the stent. The stent 51 has a mesh structure with mesh gaps 52 (i.e., the structural gaps). When the locks are connected to the prosthetic valve 50, they extend into the mesh gaps 52 in the radial direction of the prosthetic valve 50.

In other embodiments, the prosthetic valve 50 can also be provided with connecting ears (for connecting with the delivery system) to engage with the locks, and the locks grip the connecting ears when engaging with the prosthetic valve 50.

The locks are connected to the base, which are arranged around the prosthetic valve assembly area. The locks are arranged around the periphery of the prosthetic valve 50 and can synchronously extend into the mesh gaps 52, so that the prosthetic valve 50 is limited in both axial and radial directions, thereby completely griping and holding the prosthetic valve 50.

The driving part is linked to the lock and is configured to drive the lock to release the connection with the prosthetic valve 50. Relative to the base, the driving part has a first position and a relative second position.

In the first position, the locks hold the prosthetic valve 50 in the prosthetic valve assembly area, that is, the locks limit the prosthetic valve 50 in both the axial and radial directions.

In the second position, the locks release the connection with the prosthetic valve 50 and allow the prosthetic valve 50 to move out of the prosthetic valve assembly area, that is, the driving part, under the action of an external force, drives the lock to release its limitation on the prosthetic valve 50.

Based the above-mentioned structure, in the present disclosure, the prosthetic valve can be switched between the gripped state and the released state by directly applying force to the driving part, thereby rapidly assembling or disassembling the prosthetic valve through a simple structure.

Regarding the engagement between the driving part and the base, the driving part and the base can be fixedly connected with each other, and the driving part can be switched between the first position and the second position through the deformation of the driving part itself and/or the base. It can be understood that under the action of external force, the deformable portion of the driving part itself and/or the base will be linked with the lock, driving the lock to release the prosthetic valve. If the external force is removed, the prosthetic valve will be gripped again.

The driving part and the base can be alternatively movably connected with each other, and the driving part can be switched between the first position and the second position through movement relative to the base. It can be understood that the driving part can move relative to the base under the action of external force, and the driving part is linked to the lock, thereby driving the lock to release the prosthetic valve.

The base can be formed by separate pieces. The driving part is connected to the separate pieces of the base, and is switched between the first position and the second position by combining and splitting the separate pieces. It can be understood that when the separate pieces of the base are split, the relative positions between the locks are directly or indirectly changed, so that the prosthetic valve 50 can be switched between the gripped state and the released state.

In order to allow the operator to directly hold the prosthetic valve, the holder for the prosthetic valve further includes a holding handle, which is connected to the base and located on the top side of the base.

The driving part can alternatively serve as a holding handle, and the operator can directly apply force on the driving part to hold the holder, which can simplify the structure of the holder. The driving part and the holding handle can alternatively be configured separately, and both can be connected to the base respectively, thereby distinguishing the holding part and the driving part to prevent interference when applying force.

Figure 2:
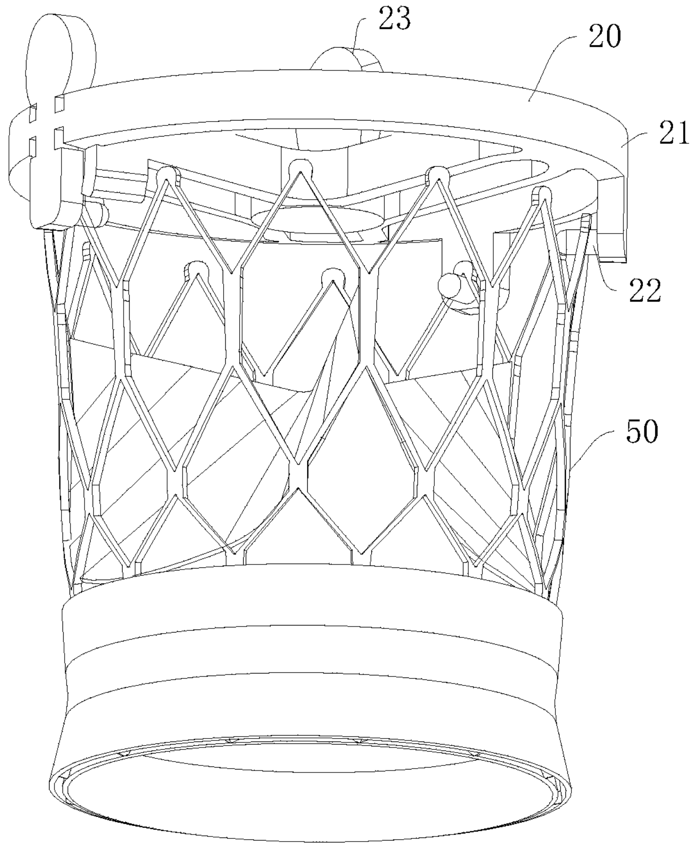
FIG. 2 is a schematic view of a holder and a prosthetic valve according to an embodiment of the present disclosure.
Figure 3:
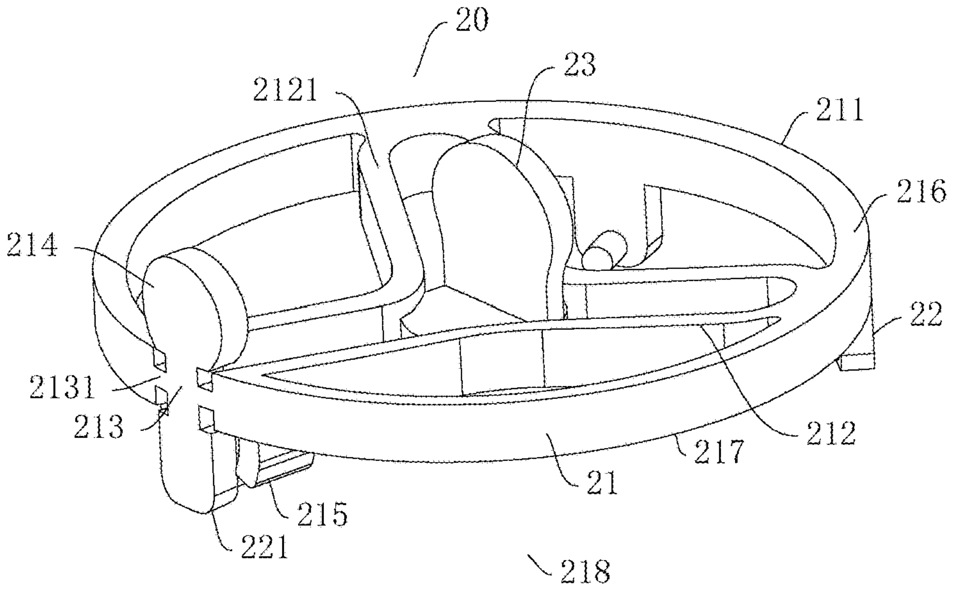
FIG. 3 is a schematic view of the holder in FIG. 2.
Figure 4:
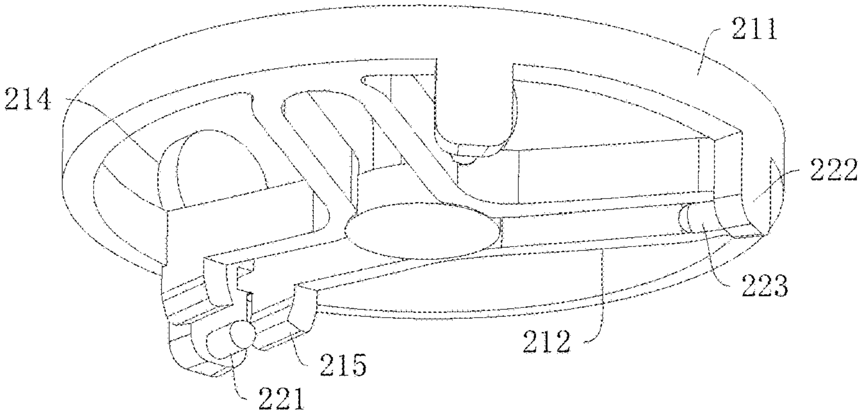
FIG. 4 is a schematic view of the holder in FIG. 1 from another perspective.

Referring to FIGS. 2 to 4, the present disclosure discloses a holder 20, which includes a base 21, locks (i.e., claws 22), a driving part, and a holding handle 23. The base 21 has a bottom side 216 and an opposing top side 217, wherein the prosthetic valve assembly area 218 is defined on the bottom side 216. The claws 22 are connected to the base 21 and are located on the bottom side 216 of the base 21, and the claws 22 are arranged around the prosthetic valve assembly area 218. The holding handle 23 is connected to the base 21 and located on the top side 217 of the base 21. The driving part is linked with the lock and is configured to drive the claw 22 to release the connection with the prosthetic valve 50.

The base 21 is mainly used to install the claws 22 and the holding handle 23, so there is no strict limitation on the shape and specific structure of the base 21. For example, the base 21 generally has a disc-shaped structure or a frame structure, and has an axial direction and a radial direction perpendicular to the axial direction in space. One axial side of the base 21 is the bottom side 216, and the other side is the top side 217.

The specific shape of the claw 22 is not strictly limited, provided that it can extend into the mesh gap 52 or grip the connecting ear. For example, the claw 22 has at least an extension section extending in the radial direction of the base 21, and the extension section limits the movement of the mesh gap 52 or the connecting ear in the axial direction of the base 21, thereby fixing the prosthetic valve 50.

The plurality of claws 22 cooperate to fix the prosthetic valve 50 in the prosthetic valve assembly area 218 on the bottom side 216 of the base 21. The quantity of claws 22 is 2, 3 or more than 4. The quantity of claws 22 in the figure is 3, and the three claws 22 are arranged at intervals in the circumferential direction of the holder 20.

In this embodiment, the base 21 includes an outer ring 211 and a plurality of transition arms 212. The claws 22 are arranged at intervals on the bottom side of the outer ring 211. The transition arms 212 extend from the inner edge of the outer ring 211 toward the central area of the base 21 and are connected with the holding handle 23. The outer ring 211 and the transition arms 212 can be formed in one or separate pieces.

The outer ring 211 has a continuous annular shape (for example, the ring in the figure), and the axial direction and radial direction of the outer ring 211 correspond to the axial direction and radial direction of the base 21 respectively.

In the axial direction of the outer ring 211, the portions of the transition arms 212 at the center of the outer ring 211 are recessed toward the bottom side of the base 21, and the holding handle 23 is located in the recess, thereby avoiding interference between the holding handle 23 and upper components.

The quantity of transition arms 212 is 2, 3 or more than 4. There are three transition arms in the figure. The transition arm includes two connecting rods 2121 arranged side by side. The adjacent connecting rods of adjacent transition arms 212 are smoothly transitionally connected near the center of the outer ring 211. The connecting rods are connected near the center of the outer ring 211 and connected to the root of the holding handle 23, while the head of the holding handle 23 extends toward the top side of the holder 20.

In order to facilitate the connection or disconnection with the prosthetic valve, in the present embodiment, one of the claws 22 is a movable claw 221. One section of the outer ring 211 is a connecting portion 213, and the driving part is a driving handle 214 arranged on the top side of the connecting portion 213. As shown in the figure, the movable claw 221 is connected to the bottom side of the connecting portion 213, and the driving handle 214 is connected to the top side of the connecting portion 213 and linked to the movable claw 221 through the connecting portion 213.

In the circumferential direction of the outer ring 211, the portion of the outer ring 211 adjacent to the connecting portion 213 is a deformable portion 2131, which allows the movable claw 221 to move relative to the outer ring 211.

The outer ring 211 is axially narrowed or radially narrowed at two sides adjacent to the connecting portion 213 to form the deformable portion 2131. For example, in the figure, the outer ring 211 is axially narrowed at two sides adjacent to the connecting portion 213 to form the deformable portion 2131.

The movable claw 221 has an initial state (in which the driving handle 214 is in the first position) and an unlocked state (in which the driving handle 214 is in the second position) relative to the outer ring 211. In the initial state, the movable claw 221 cooperates with other claws to grip and hold the prosthetic valve 50, and in the unlocked state, the movable claw 221 is separated from the corresponding mesh gap 52, which facilitates the disconnection of the prosthetic valve from the holder.

The deformable portion 2131 uses its resilience to drive the movable claw 221 to move toward the initial state to hold the prosthetic valve in the prosthetic valve assembly area. Under the action of external force, the driving handle 214 linked the movable claw 221 drives the movable claw 221 to move toward the unlocked state, in which the deformable portion 2131 is twisted and deformed and stores energy. After the force on the driving handle 214 is released, the deformable portion drives the driving handle 214 to reset itself.

In this embodiment, the base 21 is further connected to a pair of supporting arms 215. In the circumferential direction of the base 21, the supporting arms 215 in the same pair are located on two sides of the movable claw 221 to support the prosthetic valve 50. Moreover, the distance between the two supporting arms 215 avoids the movement path of the movable claw 221.

In this embodiment, the claw 22 includes a connecting arm 222 fixed to the base 21 and a claw head 223 located on the connecting arm 222 and protruding radially. The claw head 223 is used to engage with the prosthetic valve 50.

The connecting arm 222 is generally bar-shaped. One end of the connecting arm 222 is fixedly connected to the bottom side of the outer ring 211, and the other end extends toward the bottom side 216 of the base 21. In the radial direction of the outer ring 211, two sides of the connecting arm 222 are substantially flush with the inner and outer sides of the outer ring 211 respectively.

The claw head 223 is generally cylindrical, and the axis of the claw head 223 extends in the radial direction of the outer ring 211. The cross section of the claw head 223 can be circular or polygonal. One axial end of the claw head 223 is fixedly connected to the side of the connecting arm 222 facing the center of the outer ring 211, and the other end extends toward the center of the outer ring 211. When the claw head 223 is connected to the prosthetic valve 50, the connecting arm 222 is located outside the prosthetic valve 50.

There is a certain distance between the claw head 223 and the bottom side 216 of the base 21. The end of the claw head 223 is spheroidal, in order to facilitate the connection between the claw head 223 and the prosthetic valve 50 and avoid puncturing the leaflets.

The holder 20 according to this embodiment can be formed as a single piece, without need to assemble components, thereby improving the processing efficiency.

Referring to FIGS. 5 to 8, the present disclosure discloses a holder 60, which includes a base 61, locks 62 and a driving part. The base 61 has a bottom side 612 and an opposing top side 613, wherein the prosthetic valve assembly area 614 is defined on the bottom side 612. The lock 62 is connected to the base 61 and is located on the bottom side 612 of the base 61. The plurality of locks 62 are arranged around the prosthetic valve assembly area 614. The specific shape of the lock 62 is not strictly limited, and it can at least extend into the mesh gap 52 or grip the connecting ear.

In this embodiment, the base 61 has a frame structure, and the middle part 63 of the frame structure serves as a holding handle. The base 61 also includes transition arms 615 and connecting portions 611. The transition arm 615 radially extends from the middle part 63, the connecting portion 611 is the end of the transition arm 615, and the base 61 having a single frame structure can significantly enhance the structural stability of the holder.

Figure 5:
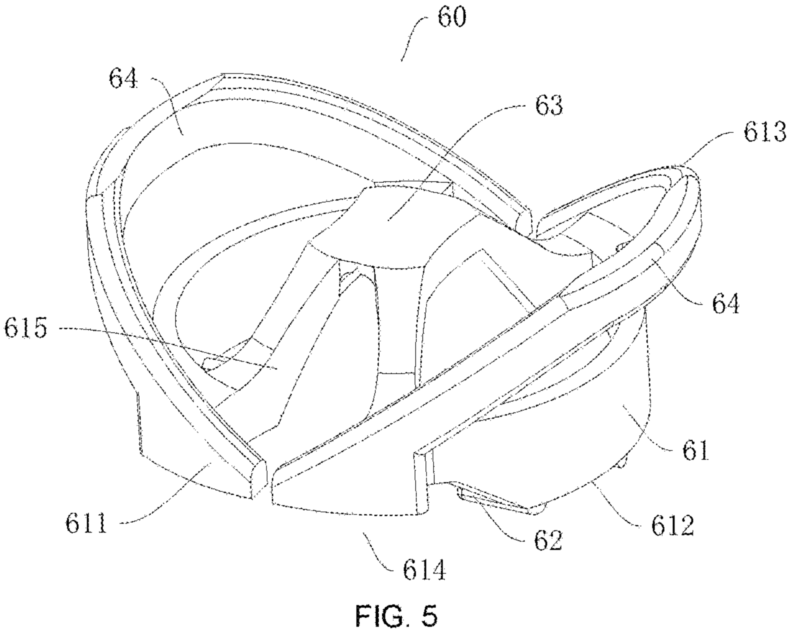
FIG. 5 is a schematic view of a holder according to an embodiment of the present disclosure.
Figure 6:
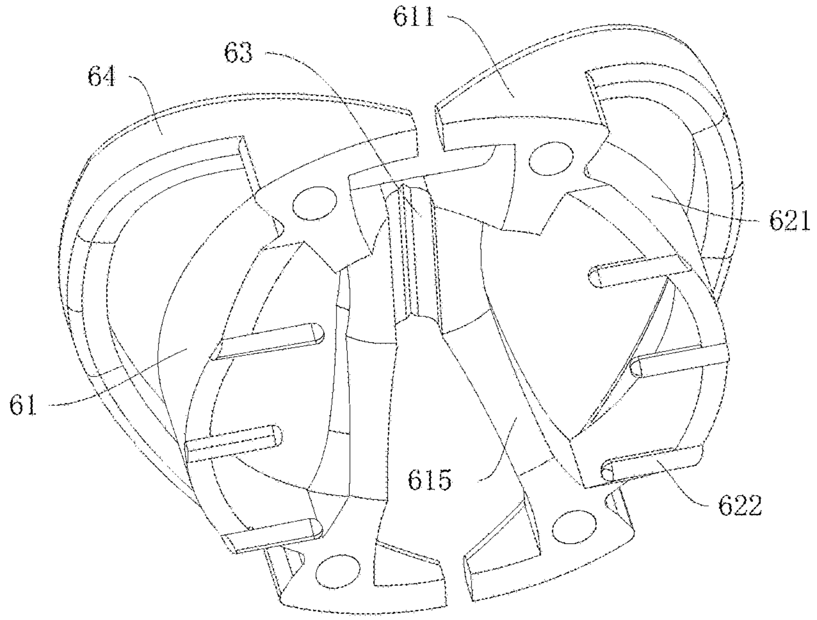
FIG. 6 is a schematic view of the holder in FIG. 5 from another perspective.
Figure 7:
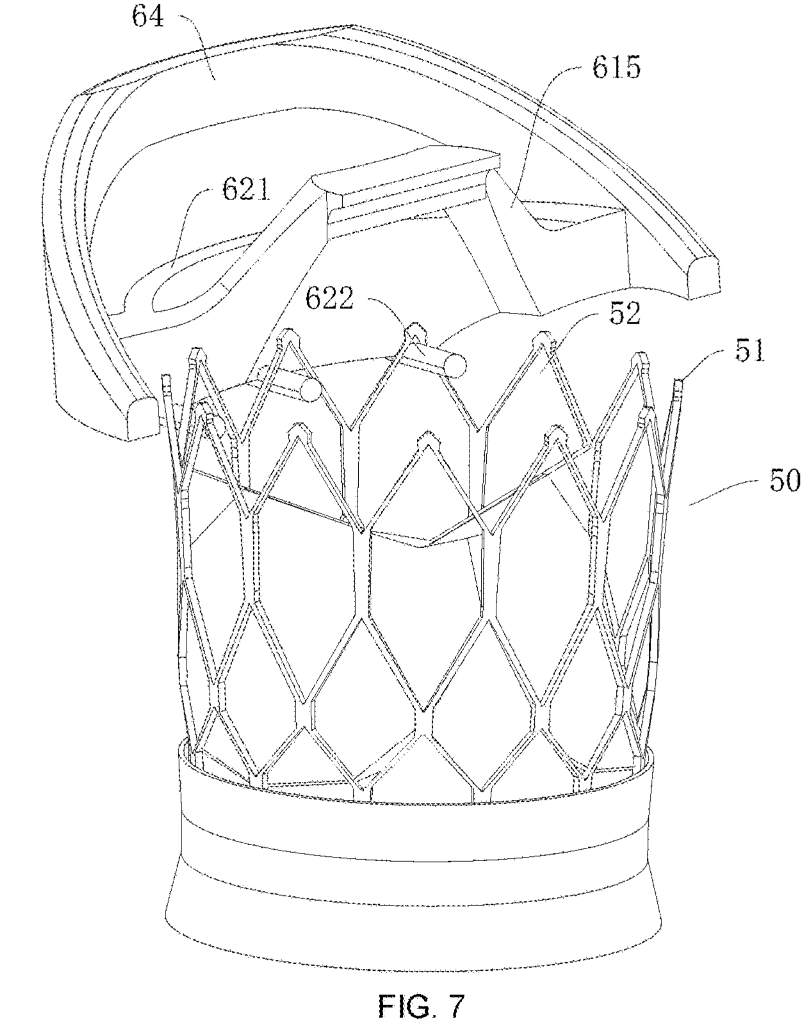
FIG. 7 is a schematic view showing the lock in FIG. 6 and the prosthetic valve.
Figure 8:
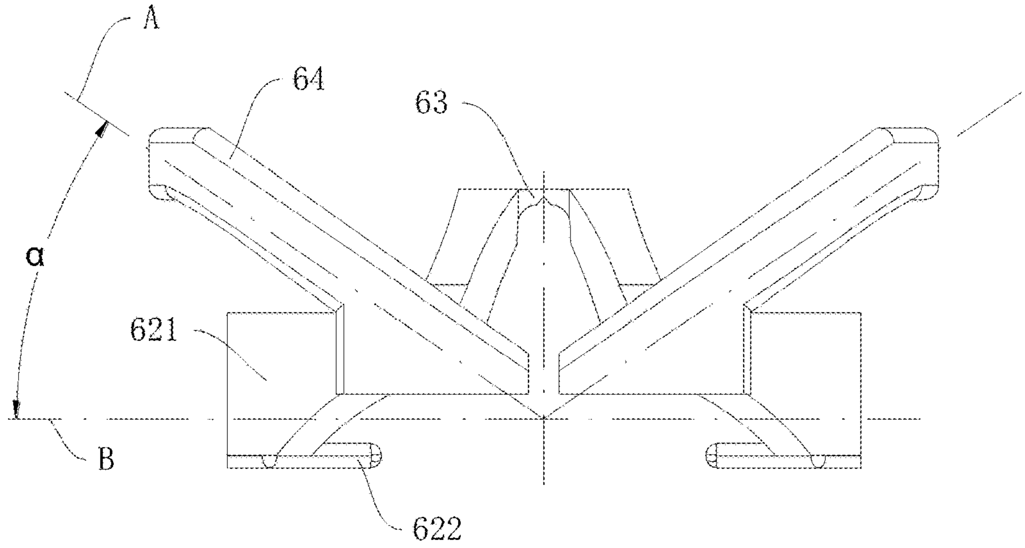
FIG. 8 is a schematic view of the holder in FIG. 5 from another perspective.
Figure 9:
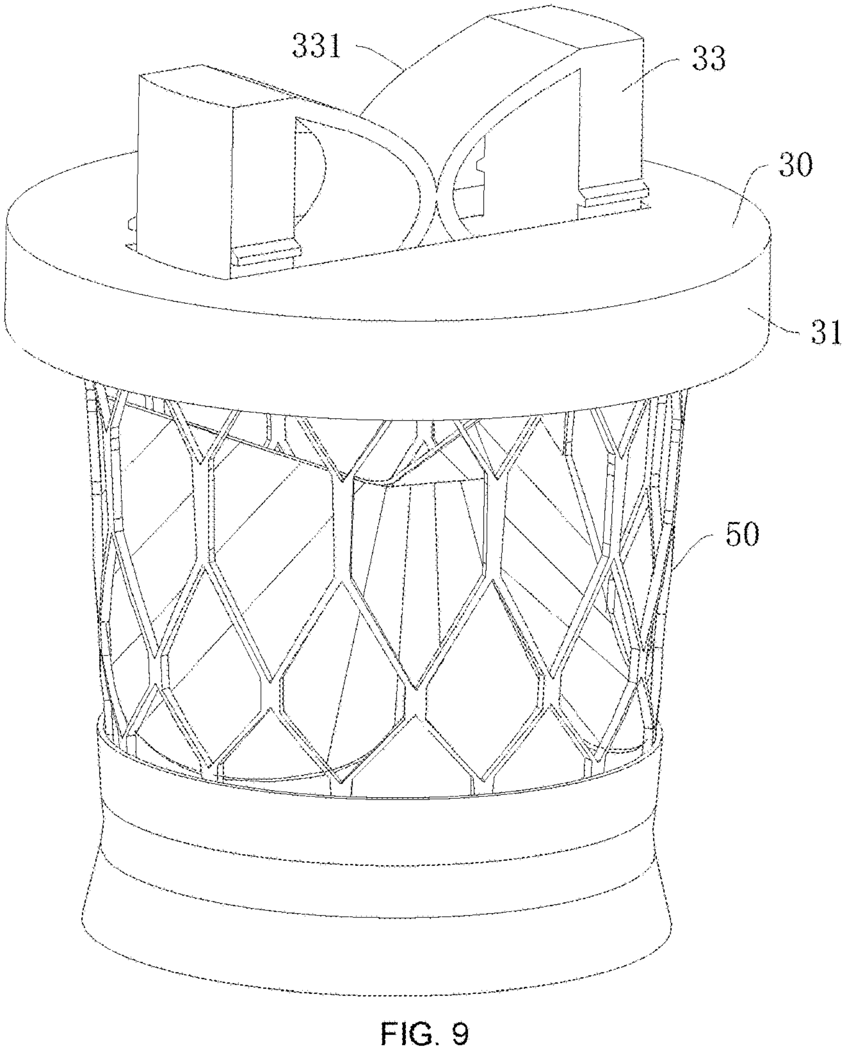
FIG. 9 is a schematic view of a holder and a prosthetic valve according to an embodiment of the present disclosure.
Figure 10:
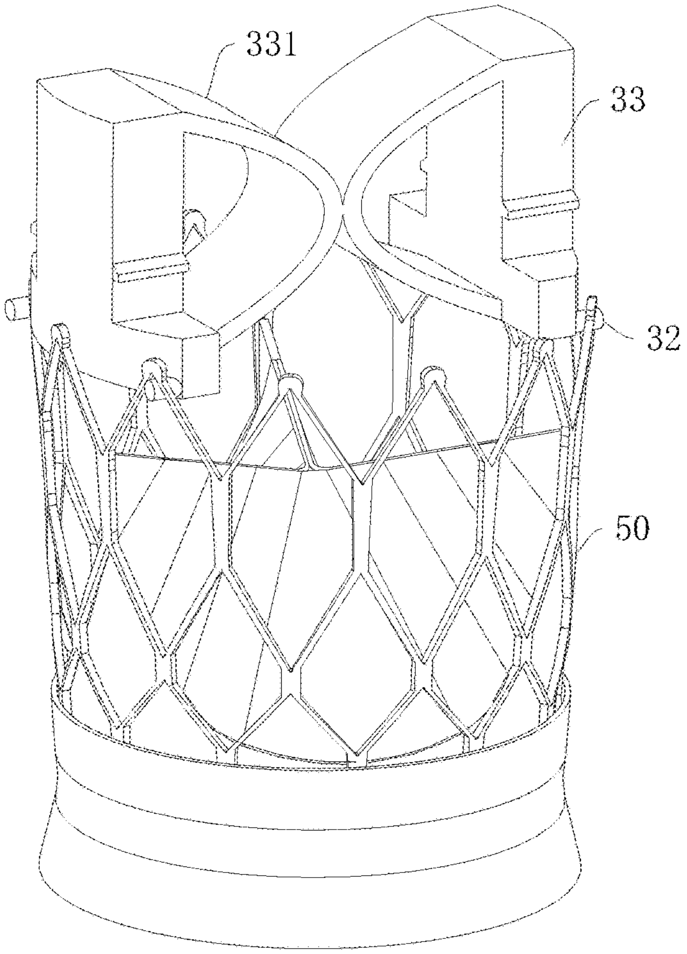
FIG. 10 is a schematic view showing the lock in FIG. 9 and the prosthetic valve.
Figure 11:
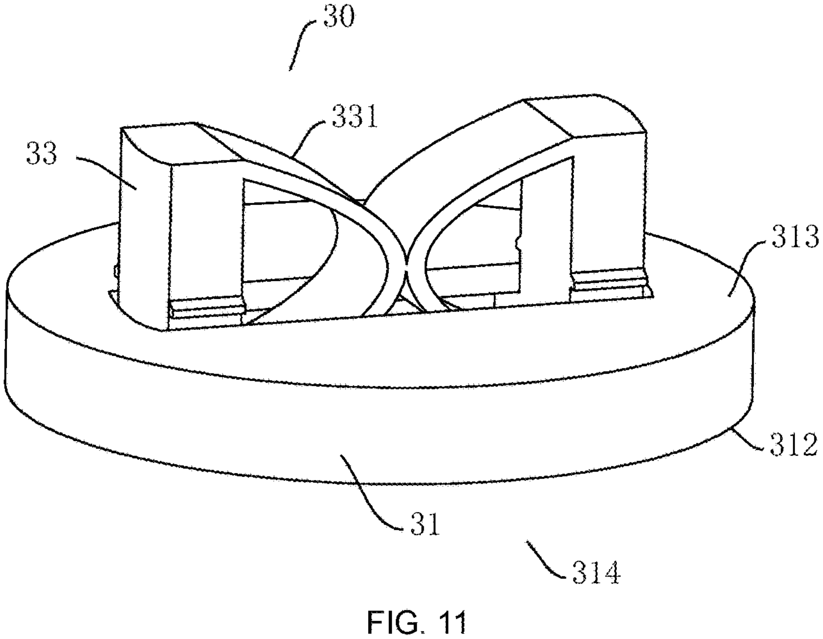
FIG. 11 is a schematic view of the holder in FIG. 9.
Figure 12:
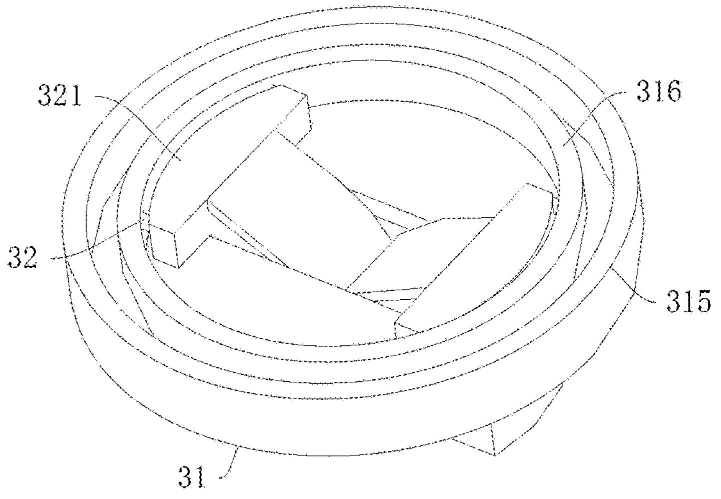
FIG. 12 is a schematic view of the holder in FIG. 9 from another perspective.
Figure 13:
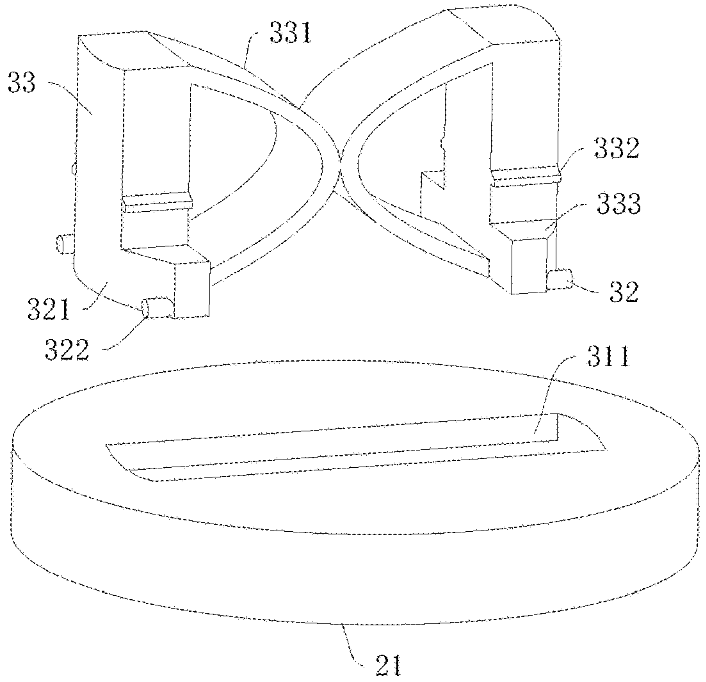
FIG. 13 is an exploded view of the holder in FIG. 11.
Figure 14:
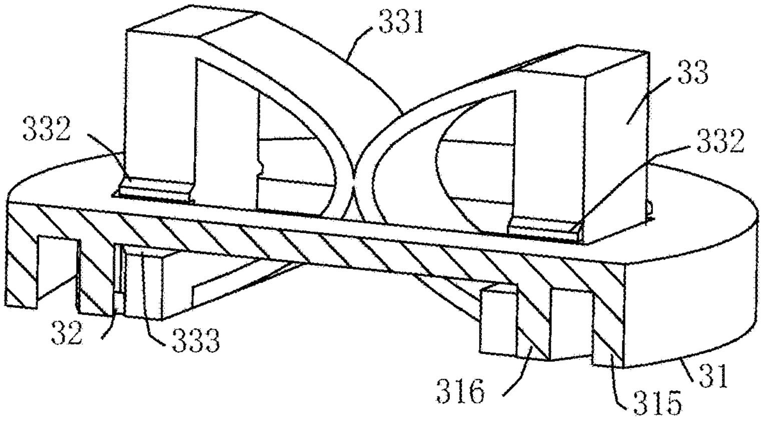
FIG. 14 is a partial cross-sectional view of the holder in FIG. 11.
Figure 15:
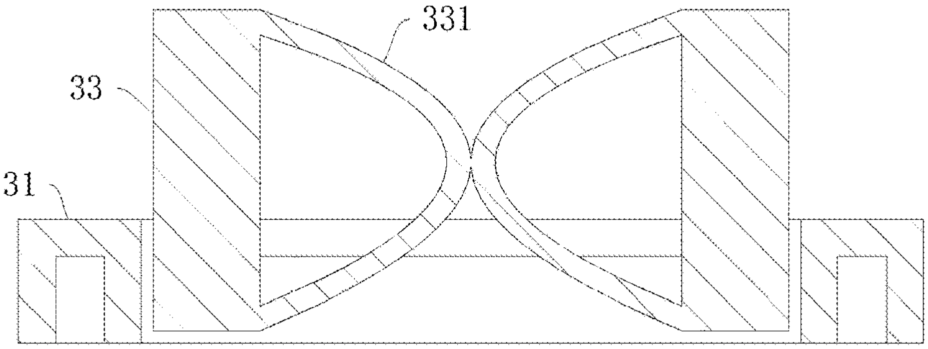
FIG. 15 is a schematic view showing the two holding handles in FIG. 11 in an initial state.
Figure 16:
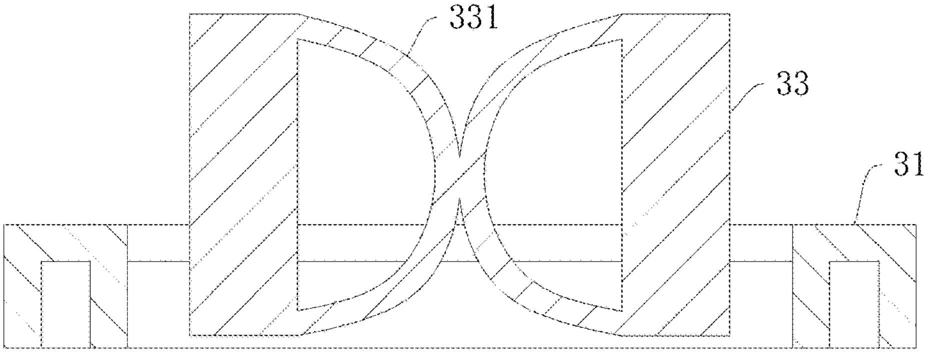
FIG. 16 is a schematic view showing the two holding handles in FIG. 11 in an unlocked state.
Figure 17:
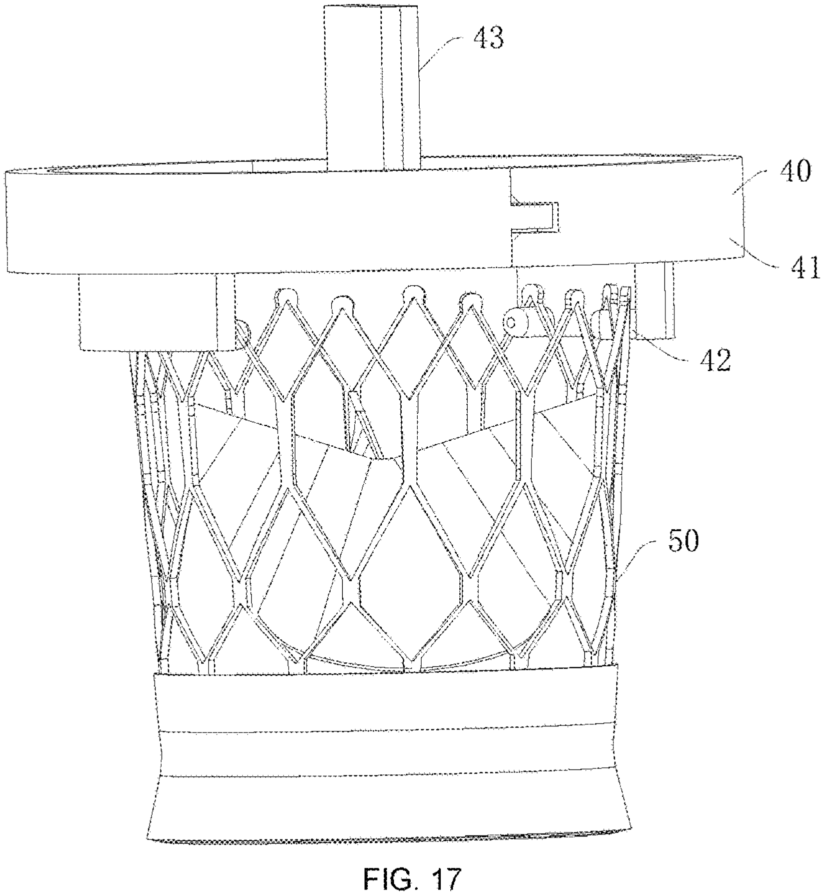
FIG. 17 is a schematic view of a holder and a prosthetic valve according to an embodiment of the present disclosure.
Figure 18:
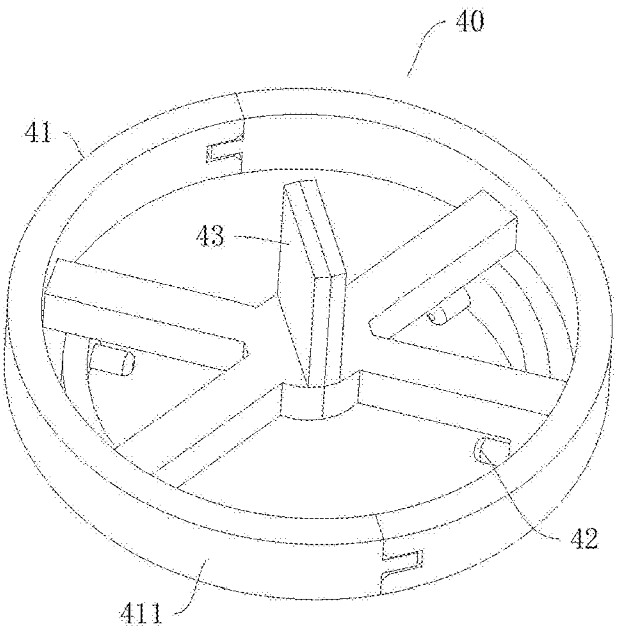
FIG. 18 is a schematic view of the holder in FIG. 17.
Figure 19:
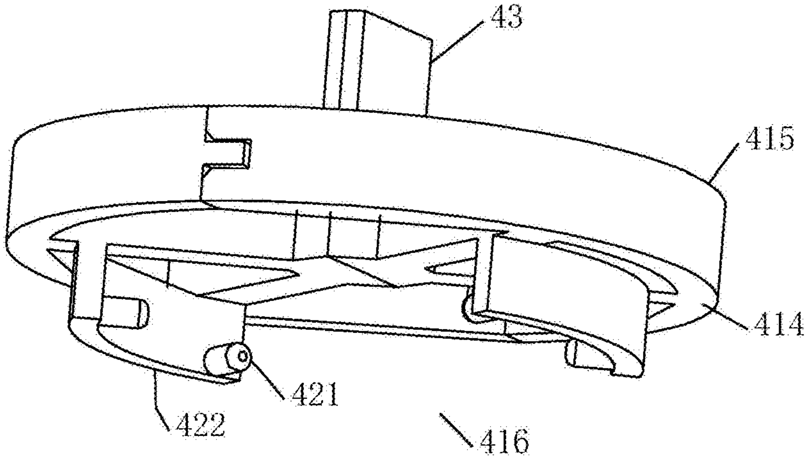
FIG. 19 is a schematic view of the holder in FIG. 17 from another perspective.
Figure 20:
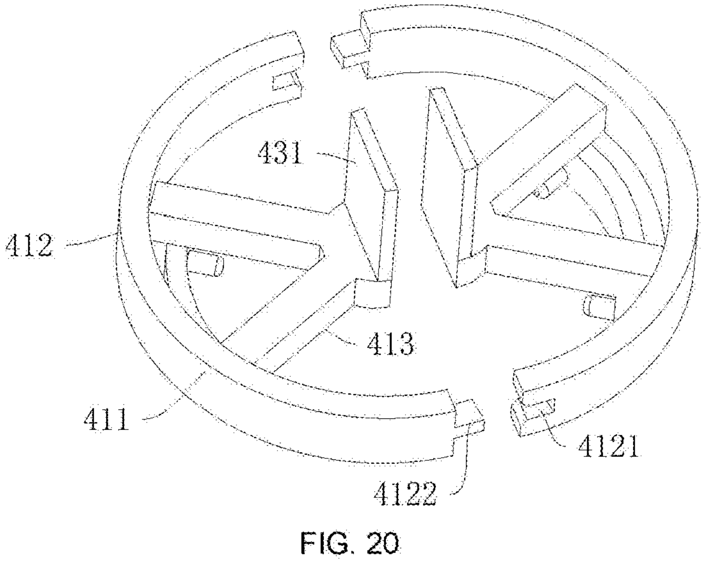
FIG. 20 is an exploded view of the holder in FIG. 17.

The transition arms 615 are divided into a plurality of groups, so that the transition arms have stronger deformation ability. Depending on the quantity of locks and a plurality of groups of transition arms, the driving part includes a plurality of driving handles 64, and each driving handle 64 is connected to the corresponding transition arms 615 in the corresponding group, so that the driving handle 64 is linked to the corresponding transition arms 615 in the corresponding group. As shown in FIG. 5 and FIG. 6, two driving handles are provided, and each driving handle corresponds to two transition arms.

The base 61 has a radial direction in space. The lock 62 includes a connecting arm 621 fixed to the connecting portions 611 and claw heads 622 located on the connecting arm 621 and protruding radially inward. The connecting arm 621 mainly functions to provide support and enhance the structural strength of the lock 62. The claw head 622 functions to engage with the prosthetic valve 50, and the claw head 622 can extend into the mesh gap 52. The connecting arm 621 is connected to the transition arms 615 in the corresponding group, so that the separate transition arms 615 are linked together.

Relative to the position of the connecting portions 611, the driving handles 64 are generally located at the top side 613 of the base, and the locks 62 are located at the bottom side 612 of the base. The operator exerts force on the driving handles at the top side of the base, to drive the locks on the bottom side, facilitating the force application.

The driving handle 64 is located at a first reference plane in space, and the connecting arm 621 is located at a second reference plane in space. The angle α between the first reference plane and the second reference plane is at least 30 degrees. The first reference plane refers to the plane A where the central axis of the driving handle 64 is located, and the second reference plane refers to the plane B where the connecting arm 621 is located in the radial direction, wherein the angle α between the two is at least 30 degrees, providing sufficient operating space. This prevents the operator from accidentally touching the bottom side of the base when applying force to the driving handles, and also facilitates the application of force by the operator.

There are two transition arms 615 in the same group, allowing for more uniform force application and enhancing the structural strength of the transition arms. The driving handle 64 is shaped in a first arc and its two ends are respectively connected to the ends of the corresponding transition arms 615. The connecting arm 621 is shaped in a second arc and its two ends are respectively connected to the ends of the corresponding transition arms 615. Therefore, the driving handle 64, the transition arms 615, and the connecting arm 621 are linked together stably.

In the first position, all the connecting arms are coplanar and surround the prosthetic valve assembly area 614, and the tops of the driving handles 64 are far away from each other. The locks 62 are in the initial state and extend into the mesh gaps 52 to grip the prosthetic valve 50 stably and hold the prosthetic valve 50 in the prosthetic valve assembly area 614.

When unlocking, the operator applies force to the driving handles 64, and the tops of the driving handles 64 approach each other to the second position, driving the connecting arms 621 away from the prosthetic valve 50, so that the locks 62 are separated from the mesh gaps 52 to enter the unlocked state and allow the prosthetic valve 50 to move out of the prosthetic valve assembly area 614.

Referring to FIGS. 9 to 16, the present disclosure discloses a holder 30, which includes a base 31, locks (i.e., claws 32) and driving parts 33. The base 31 has a bottom side 312 and an opposing top side 313, wherein the prosthetic valve assembly area 314 is defined on the bottom side 312. The claws 32 are connected to the base 31 and are located on the bottom side 312 of the base 31. The plurality of claws 32 are arranged around the prosthetic valve assembly area 314. The driving parts 33 are connected to the base 31 and located on the top side 313 of the base 31. The driving parts are linked with the claws 32. Relative to the base 31, the driving parts have a first position (i.e., the initial state in which the driving parts are not suffered from an external force) and a relative second position (i.e., the unlocked state in which the driving parts are suffered from an external force).

In this embodiment, the base 31 defines an installation through-hole 311. There are two driving parts 33 which are pillar-shaped. The driving parts pass through the installation through-hole 311 respectively. The part of the driving part 33 on the top side of the base 31 can also serve as a holding handle. A resilient element 331 is provided between the two driving parts 33 to adapt to the relative movement of the two driving parts 33 and to drive the two driving parts 33 to reset. The claw 32 is fixed to the corresponding driving part 33.

The installation through-hole 311 is open to the top side 313 and the bottom side 312 of the base 31. The installation through-hole 311 is elongated and has a length direction and a width direction in space. Two ends of the installation through-hole 311 in the length direction can limit the reset position of the two driving parts 33.

All the claws 32 are divided into two groups, with each group provided on a corresponding driving part 33, and the two groups of claws can switch between the initial state and the unlocked state. In the initial state, the two driving parts 33 are respectively located at the two ends of the installation through-hole 311 in the length direction under the action of the resilient element 331, and the two groups of claws are relatively far away from each other and support and hold the prosthetic valve 50 from the inside to the outside in the radial direction of the prosthetic valve 50.

When unlocking, the two driving parts 33 approach each other or tilt to the second position so that the claws 32 move inward in the radial direction of the prosthetic valve 50, that is, the two groups of claws are relatively close and separate from the mesh gaps 52 of the prosthetic valve 50, thereby disconnecting the prosthetic valve 50 from the holder.

The resilient element 331 is mainly used to reset the two driving parts 33 to the first position. For example, the resilient element 331 can have a deformable frame structure. The resilient element 331 and the two driving parts 33 can be formed in a single piece. In the figure, the resilient element 331 is roughly X-shaped, and the two ends of the X-shaped resilient element 331 one each side are respectively connected to the top side and the bottom side of the corresponding driving part 33.

The two driving parts 33 are slidably matched with the installation through-hole 311 in the length direction of the installation through-hole 311. In order to prevent the driving part 33 from deviating in the thickness direction of the base 31, the driving part 33 is provided with a limiting tooth 332 located at the top side 313 of the base 31 and a step structure 333 on the claw 32 located at the bottom side 312 of the base 31. The limiting tooth 332 and the step structure 333 cooperate with each other to limit the driving part 33.

In this embodiment, the claw 32 includes a connecting arm 321 and a claw head 322. The connecting arm 321 is fixed to the portion of the driving part 33 at the bottom side 312 of the base 31. The claw head 322 is located on the connecting arm 321 and protrudes radially. The claw head 322 is configured to engage with the prosthetic valve 50.

The quantity of the claws 32 fixed on each driving part 33 is 2, 3 or 4 or more, depending on the quantity of the claw heads 322 (the quantity of the claws 32 in the figure is 2). The claw head 322 is roughly cylindrical, and the axis of the claw head 322 extends in the radial direction of the outer ring of the base 31. One axial end of the claw head 322 is fixedly connected to the side of the connecting arm 321 facing away from the center of the base 31, and the other end extends away from the center of the base 31. The cross section of the claw head 322 can be circular or polygonal.

The connecting arms 321 of the claws 32 are connected with each other to form an arc-shaped rib, and the arc-shaped rib is fixed to the bottom side of the driving part 33. In the width direction of the installation through-hole 311, the size of the arc-shaped rib is larger than the size of the driving part 33, so as to form the step structures 333 between the driving part 33 and the arc-shaped rib. When the claw heads 322 are connected to the prosthetic valve 50, the arc-shaped ribs are located inside the prosthetic valve 50.

The outer periphery of the base 31 is provided with a flange 315 extending toward the bottom side 312 of the base 31. The flange 315 is used to enhance the structural strength of the base 31. The flange 315 has a continuous ring shape.

The bottom side 312 of the base 31 is further provided with a block 316. In the initial state, the ends of the claw heads 322 contact the block 316, thereby restricting the prosthetic valve 50 on the claw heads. The block 316 has a continuous ring shape. The bottom side of the flange 315 is flush with the bottom side of the block 316.

Referring to FIGS. 17 to 20, the present disclosure discloses a holder 40, which includes a base 41, locks (i.e., claws 42) and a driving part 43. The base 41 has a bottom side 414 and an opposing top side 415, wherein the prosthetic valve assembly area 416 is defined on the bottom side 414. The claws 42 are connected to the base 41 and are located on the bottom side 414 of the base 41, and the plurality of claws 42 surround the prosthetic valve assembly area 416. The driving part 43 is connected to the base 41 and located on the top side 415 of the base 41. The driving part 43 is linked with the claws 42, and relative to the base 41, the driving part has a first position (i.e., the initial state in which the driving part is not suffered from an external force) and a relative second position (i.e., the unlocked state in which the driving part is suffered from an external force). In this embodiment, the base 41 is formed by separate pieces, including a plurality of base units 411 that fit with each other in the radial direction of the base 41. The base units 411 can be connected by plugging or other methods. The claws 42 are distributed on the base units 411.

The quantity of the base units 411 can be 2 or more than 3. The shape and size of the base units 411 can be the same, which can improve the degree of standardization. In the following embodiments, two base units 411 as shown in the figure are explained as example.

Each base unit 411 includes an outer ring 412 and a transition arm 413. The end surface of the outer ring 412 in the circumferential direction is provided with an insertion fitting for engaging with the other base unit 411. The transition arm 413 extends from the inner edge of the outer ring 412 toward the central area.

The outer ring 412 is in the shape of a fan ring, and the axial direction and radial direction of the outer ring 412 correspond to the axial direction and radial direction of the base 41 respectively. In the circumferential direction of the base 41, the corresponding end surfaces of the outer rings 412 of two adjacent base units 411 are in contact with each other.

In the circumferential direction of the base 41, one of the outer rings 412 of two adjacent base units 411 defines a slot 4121 on the end surface thereof, and the other is provided with an insertion block 4122 that extends into the slot 4121 on the end surface thereof. The depth direction of the slot 4121 extends in the circumferential direction of the outer ring 412, and the slot 4121 is open on both sides of the outer ring 412 in the radial direction.

The transition arm 413 includes a plurality of connectors. One end of each connector is connected to the inner edge of the outer ring 412, and the other end extends toward the geometric center of the base 41. The connectors are connected together at the geometric center of the base 41. The quantity of connectors in the figure is 2.

The driving part 43 can also serve as a holding handle. The driving part 43 generally includes a plurality of handle units 431. Each handle unit 431 corresponds to a base unit 411 and is connected to the end of the corresponding transition arm 413 facing the geometric center of the base 41. The switching of the two relative positions of the driving part corresponds to the switching of the states of the claws. All the claws 42 are divided into two groups, with each group provided on a corresponding base unit 411, and the two groups of claws 42 switch between the relative initial and unlocked states. In the initial state, the two base units 411 fit with each other, and the claws 42 cooperate with each other to grip the prosthetic valve 50. The handle unit 431 is roughly plate-shaped, and the two handle units fit with each other when the two base units 411 fit with each other.

In the unlocked state, the two base units 411 move far away from each other to drive the two groups of claws 42 to disengage from the corresponding mesh gaps 52, facilitating the separation of the prosthetic valve 50 from the holder 40.

In this embodiment, the claw 42 includes a connecting arm and a claw head 421 protruding radially and located on the connecting arm. The claw head 421 is used to engage with the prosthetic valve 50.

On the same base unit 411, the connecting arms of all claws 42 are fixed to the outer ring 412 or the transition arm 413. The quantity of claws 42 on the same base unit 411 is 2, 3 or 4, depending on the quantity of claw heads 421. In the figure, the quantity of claws 42 on the same base unit 411 is two.

The claw head 421 is generally columnar, and the axis of the claw head 421 extends in the radial direction of the outer ring 412. One axial end of the claw head 421 is fixedly connected to the side of the connecting arm facing the center of the base 41, and the other end extends toward the center of the base 41. When the claw heads 421 grip the prosthetic valve 50, the connecting arms are located on the outer side of the prosthetic valve 50. The cross section of the claw head 421 can be circular or polygonal.

There is a certain distance between the claw head 421 and the bottom side 414 of the base 41. The end of the claw head 421 has a spheroidal shape, to facilitate the connection of the claw head 421 with the prosthetic valve 50.

On the same base unit 411, the connecting arms of all the claws 42 are connected with each other to form an arc-shaped rib 422, which is fixed to the transition arm 413 and is closer to the geometric center of the base 41 than the outer ring 412. The arc-shaped rib 422 and the outer ring 412 are formed in one or separate pieces.

Referring to FIGS. 21 to 27, the present disclosure discloses a holder 80 for a prosthetic valve 50, comprising:

- a base 81, which defines engagement openings 814 for the prosthetic valve 50 to pass through;
- locks 82, which are movably mounted on the base 81 and have an initial state and an unlocked state relative to the base 81, which are configured to restrict the prosthetic valve 50 passing through the engagement openings 814 in the initial state, and allow the prosthetic valve 50 to disengage from the engagement openings 814 in the unlocked state; and
- driving parts 83, which are movably mounted on the base 81 and are linked with the locks 82 to drive the locks 82 to move toward the unlocked state.

Figure 21:
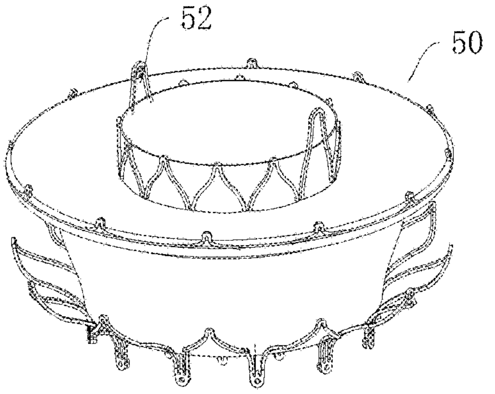
FIG. 21 is a schematic view of a prosthetic valve according to an embodiment of the present disclosure.
Figure 22:
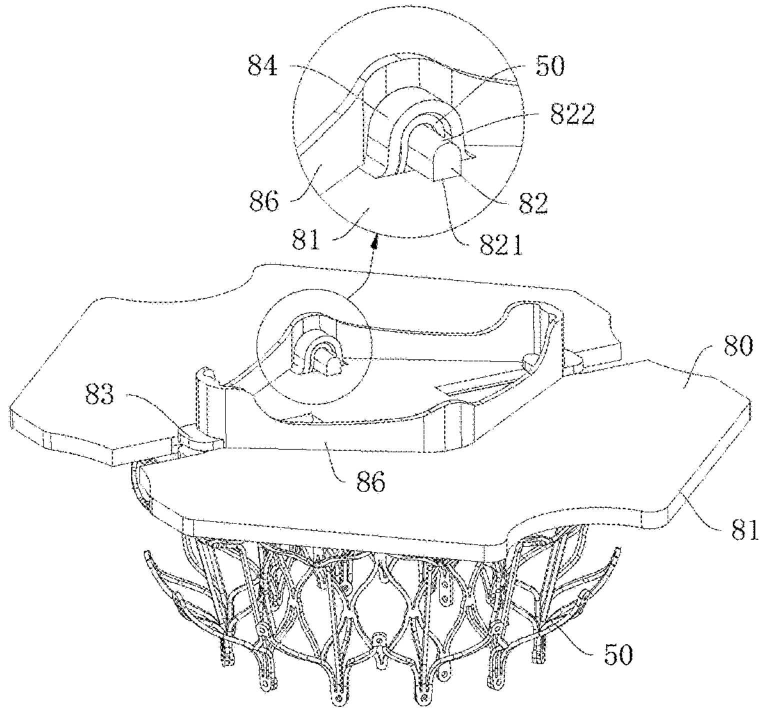
FIG. 22 is a schematic view of a holder and a prosthetic valve according to an embodiment of the present disclosure.

Taking the prosthetic valve 50 (for example, a tricuspid valve) in FIG. 21 as an example, the prosthetic valve 50 includes a cylindrical stent. The stent can generally be formed by cutting or weaving. In order to achieve radial deformation, most stents have a mesh structure. The lock 82 mainly functions to engage with the mesh gap 52 of the prosthetic valve. In other embodiments, the prosthetic valve 50 can be provided with connecting ears for engaging with the locks 82.

The base 81 is mainly used to fix and support the prosthetic valve 50, and components such as the locks 82 and the driving parts 83 are also installed on the base 81. The base 81 is used to support the components, so it requires a certain structural strength. There is no strict limitation on the shape and specific structure of the base 81. As shown in the figure, the base 81 is plate-shaped, having a top side 811 and a bottom side 812 opposite to each other in the thickness direction, wherein the prosthetic valve assembly area 813 is defined on the bottom side 812.

The engagement opening 814 is open to at least the bottom side 812 of the base 81 so that at least part of the prosthetic valve 50 can enter and exit the engagement opening 814. When the base 81 engages with the prosthetic valve 50, the engagement openings 814 can reduce the overall length of the base 81 and the prosthetic valve 50 in the axial direction of the prosthetic valve 50.

The specific shape of the lock 82 is not strictly limited, and the lock 82 can at least extend into the mesh gap 52 of the prosthetic valve 50 or grip the connecting ear. For example, the lock 82 at least has an extension section extending in the radial direction of the prosthetic valve 50, and the extension section limits the movement of the mesh gap 52 or the connecting ear in the thickness direction of the base 81, thereby fixing the prosthetic valve 50 at the prosthetic valve assembly area 813.

The initial state and the unlocked state of the locks 82 correspond to two relative positions of the locks 82. In the initial state, the lock 82 extends into the mesh gap 52 or grips the connecting ear to fix the prosthetic valve 50. In the unlocked state, the lock 82 is disengaged from the mesh gap 52 or the connecting ear to release the prosthetic valve 50.

The driving parts 83 are convenient for the operator to hold. By controlling the driving parts 83, the locks 82 are driven to switch between the initial state (i.e., the first position) and the unlocked state (i.e., the second position). For example, the driving part 83 protrudes from the top side 811 of the base 81 to facilitate the manipulation of the driving part 83. In this embodiment, the engagement opening 814 on the base 81 is open to the bottom side 812 and the top side 811 of the base 81, and part of the prosthetic valve 50 passes through the engagement opening 814 and is located on the top side of the base 81. The lock 82 is located on the top side 811 of the base 81 and can engage with the part of the prosthetic valve 50 that passes through the engagement opening 814.

The plurality of engagement openings 814 are distributed around the prosthetic valve 50. The locks 82 correspond to the engagement openings 814 one by one, and engage with the mesh gaps 52 or connecting ears of the prosthetic valve 50 that passes through the engagement openings 814, thereby stably fixing the prosthetic valve 50 at the prosthetic valve assembly area 813 on the bottom side 812 of the base 81.

As shown in the figure, the quantity of locks 82 and the quantity of engagement openings 814 are both 2, 3 or 4 or more. The following embodiments will be explained taking two locks 82 and two engagement openings 814 as shown in the figure as example. The two engagement openings 814 are respectively located on two radial sides of the prosthetic valve 50. Each engagement opening 814 has a length direction and a width direction perpendicular to the length direction, and the width direction of each engagement opening 814 is consistent with the radial direction of the prosthetic valve 50.

In this embodiment, the lock 82 is rod-shaped, and its length spans at least across the engagement opening 814. The axis of the lock 82 is parallel to the width direction of the engagement opening 814, and the axial length of the lock 82 is at least greater than the width of the engagement opening 814. In the initial state, the two ends of the lock 82 are respectively located on two opposite sides of the engagement opening 814. For engagement, one end of the lock can be grooved to clamp the prosthetic valve 50.

The outer side wall of the lock 82 includes a planar surface 821 and an arc surface 822 that are opposite to each other. The planar surface 821 fits the base 81, and the arc surface 822 contacts the mesh gap 52 or the connecting ear to increase the contact surface with the mesh gap 52 or the connecting ear. As shown in the figure, the outer contour of the cross section of the lock 82 is U-shaped, and the opening of the U shape is closed, wherein the arc segment of the U shape corresponds to the cross section of the arc surface 822, and the opened end of the U shape which is closed corresponds to the cross section of the planar surface 821.

In this embodiment, the top surface of the base 81 is fixedly provided with lock seats 84 adjacent to the engagement openings 814. The lock 82 is inserted into the corresponding lock seat 84 in the initial state. The lock seat 84 can prevent the lock 82 from tilting relative to the top side 811 of the base 81. The lock seats 84 and the base 81 are formed in a single piece.

The lock seat 84 has an insertion hole 85 for accommodating the lock 82. The insertion hole 85 is designed to conveniently allow the lock 82 to be inserted into the lock seat 84. The insertion hole 85 can be formed by the lock seat 84 itself or surrounded by the lock seat 84 and the base 81.

For example, the lock seat 84 is disposed across the engagement opening 814 and surrounds the insertion hole 85 communicated with the engagement opening 814. The part of the prosthetic valve 50 that passes through the engagement opening 814 enters the insertion hole 85, and the lock 82 extends into the insertion hole 85 and engages with the prosthetic valve 50 in the insertion hole.

As shown in the figure, the lock seat 84 is roughly U-shaped, with the two ends of the U shape on the open side respectively located on two opposite sides in the length direction of the engagement opening 814, and the area within the U shape forms the insertion hole 85.

In this embodiment, the driving parts 83 and the locks 82 can be directly or indirectly linked. For example, the driving parts 83 can be connected to the locks 82 via a transmission arm 86, and the driving parts 83 drive the locks 82 to switch from the initial state to the unlocked state via the transmission arm 86. The transmission arm 86, the driving parts 83 and the locks 82 can be formed in a single piece.

In this embodiment, the transmission arm 86 is belt-shaped and generally forms as a deformable quadrilateral. The driving parts 83 are arranged in pair at diagonal positions of the quadrilateral, and the locks 82 are arranged in pair at the other diagonal positions of the quadrilateral.

The driving parts 83, the locks 82 and the transmission arm 86 are all on the same side (top side 811) of the base 81, and the transmission arm 86 allows the driving parts 83 and the locks 82 to move in the same plane, so as to reduce the overall thickness. The movement paths of the two locks 82 are perpendicular to the movement paths of the two driving parts 83.

The quadrilateral in the figure is a rhombus. When the transmission arm 86 switches between the unlocked state and the initial state, the two locks 82 can move synchronously, with a high transmission efficiency.

The transmission arm 86 is connected to the ends of the locks 82 facing away from the prosthetic valve 50. When the locks 82 are in the initial state, the inner side of the transmission arm 86 contacts the lock seats 84.

Figure 23:
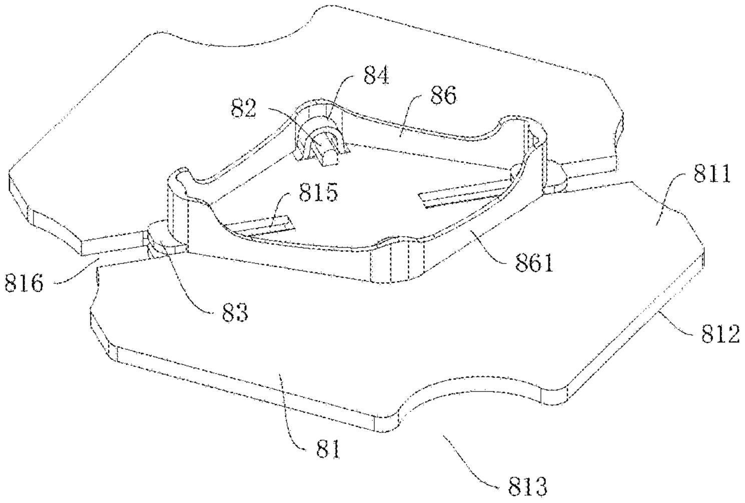
FIG. 23 is a schematic view of the holder in FIG. 22.
Figure 24:
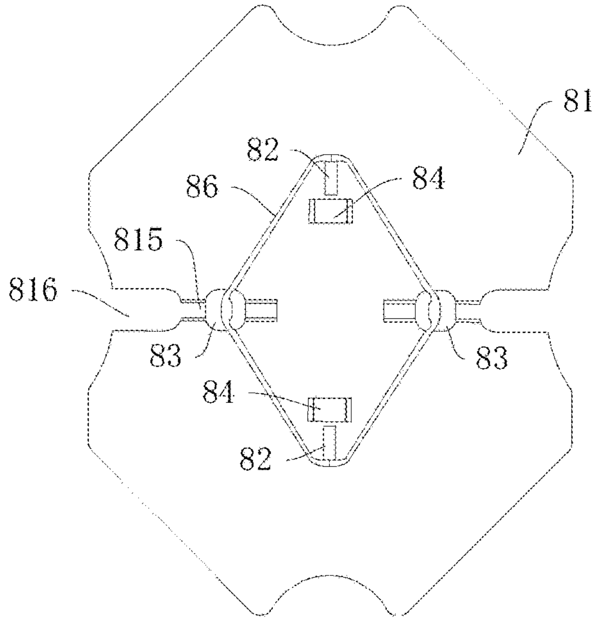
FIG. 24 is a schematic view of the holder in FIG. 22 in an unlocked state.
Figure 25:
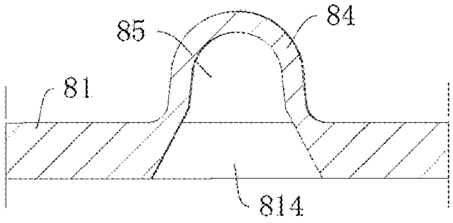
FIG. 25 is a partial cross-sectional view of the base in FIG. 22.
Figure 26:
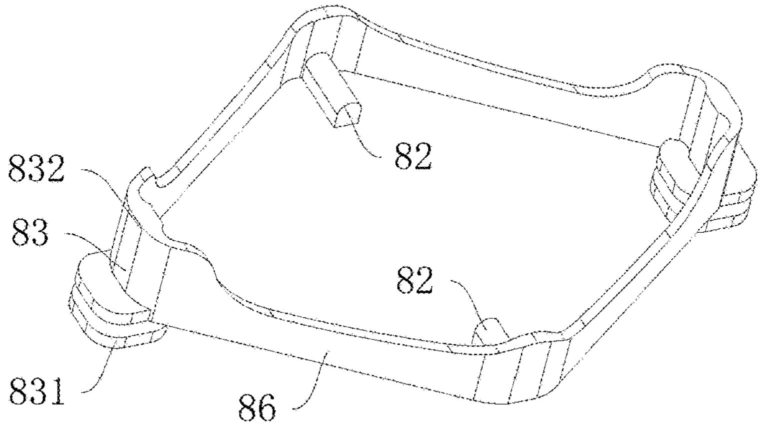
FIG. 26 is a schematic view of the locks, the driving parts and the connecting arm in FIG. 22.
Figure 27:
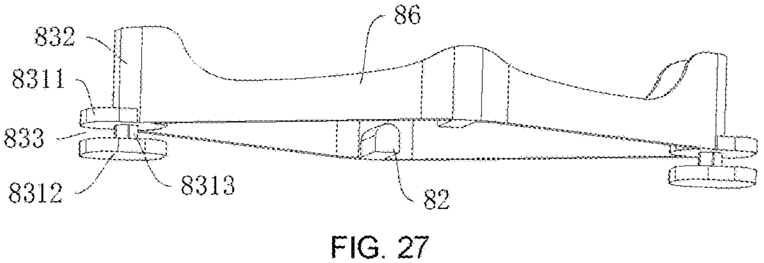
FIG. 27 is a schematic view of the locks, the driving parts and the connecting arm in FIG. 22 from another perspective.

As shown in FIG. 23 and FIG. 24, the locks 82 have an initial state and an unlocked state. In the initial state, the lock 82 is inserted into the insertion hole 85 of the lock seat 84 (the lock 82 is in the initial state) and extends into the mesh gap 52 or the connecting ear.

In the unlocked state, the two driving parts 83 move toward each other, and the two driving parts 83 drive the locks 82 to move away from each other through the transmission arm 86 until the locks 82 are disengaged from the insertion holes 85 (the locks 82 are in the unlocked state), thereby disconnecting the prosthetic valve from the base 81. The operator can use one hand to move the two driving parts 83 toward each other, thereby reducing the difficulty of operating the holder 80.

The transmission arm 86 uses resilience to drive the locks 82 toward the initial state. When the two driving parts 83 move toward each other, the locks 82 are driven by the transmission arm 86 to move toward the unlocked state, in which state the transmission arm 86 is twisted and deformed and stores energy. After the force on the driving parts 83 is released, the transmission arm 86 reset itself to drive the locks 82 to switch from the unlocked state to the initial state.

The transmission arm 86 includes four arm units 861. Each arm unit 861 has a length direction, one end of the arm unit 861 in the length direction is connected to the driving part 83, and the other end is connected to the lock 82. The connections between the two ends of the arm unit 861 and the driving part 83 and the lock 82 are deformable.

The driving part 83 includes a root 831 and a handle 832 extending from the root 831 toward the top side 811 of the base 81. The root 831 is slidably connected to the base 81. The base 81 can be provided with guide rails matching with the roots 831. There is no strict limitation on the shape and structure of the guide rail. The guide rail can be a groove or ridge extending in a predetermined direction on the base 81, or a guide rod. In order to adapt to the guide rail, for example, in the case where the guide rail is a guide rod, the corresponding root 831 can be a sliding sleeve mounted on the guide rod, and in the case where the guide rail is an elongate groove, the corresponding root 831 can be a supported block or supported bar embedded in the elongate groove.

As shown in the figure, guide grooves 815 are defined on the base 81. Two opposite sides of the root 831 define clamping grooves 833, the groove walls of the guide groove 815 are received in the clamping grooves 833 on the corresponding sides respectively, and the guide groove 815 is used to guide the movement path of the driving part 83. One end of the guide groove 815 points to the middle area of the base 81, and the other end extends to and opens to the edge of the base 81, to facilitate the engagement of the clamping grooves 833 of the root 831 with the groove walls of the guide groove 815.

There are two guide grooves 815, and the extension directions of the two guide grooves 815 are parallel to each other. The two guide grooves 815 are arranged in the radial direction of the prosthetic valve 50, and the two guide grooves 815 are not communicated with each other. The opening of the guide groove 815 has a flared section 816 for guiding the root 831 to enter the guide groove 815.

The root 831 includes a first limiting portion 8311 on the top side 811 of the base 81, a second limiting portion 8312 on the bottom side 812 of the base 81, and a connecting portion connecting the first limiting portion 8311 and the second limiting portion 8312. The first limiting portion 8311 is connected with the handle 832. The first limiting portion 8311 and the second limiting portion 8312 cooperate with each other to limit the connection position of the root 831 with the base 81. The first limiting portion 8311, the second limiting portion 8312 and the connecting portion 8313 define the clamping grooves 833.

In the figure, the first limiting portion 8311 and the second limiting portion 8312 are both plate-shaped, and the connecting portion 8313 is pillar-shaped. The first limiting portion 8311 contacts the top side 811 of the base 81, and the second limiting portion 8312 contacts the bottom side 812 of the base 81. Two ends of the connecting portion 8313 are respectively connected to the middle portions of the first limiting portion 8311 and the second limiting portion 8312.

Figure 28:
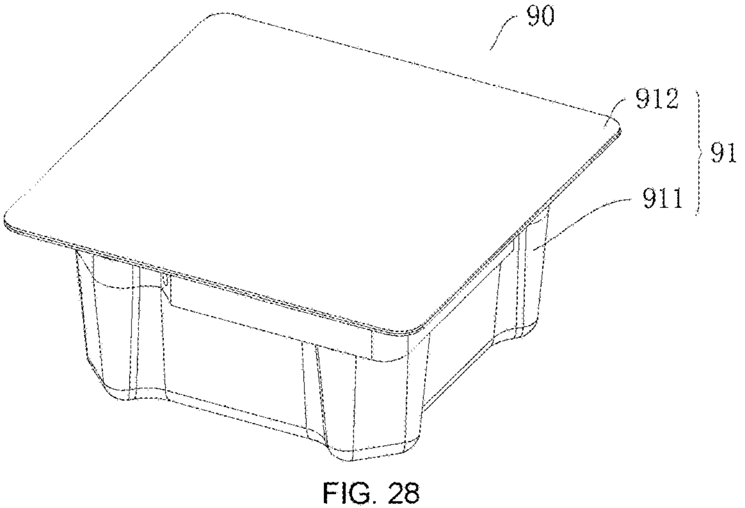
FIG. 28 is a schematic view of a packaging box according to an embodiment of the present disclosure.
Figure 29:
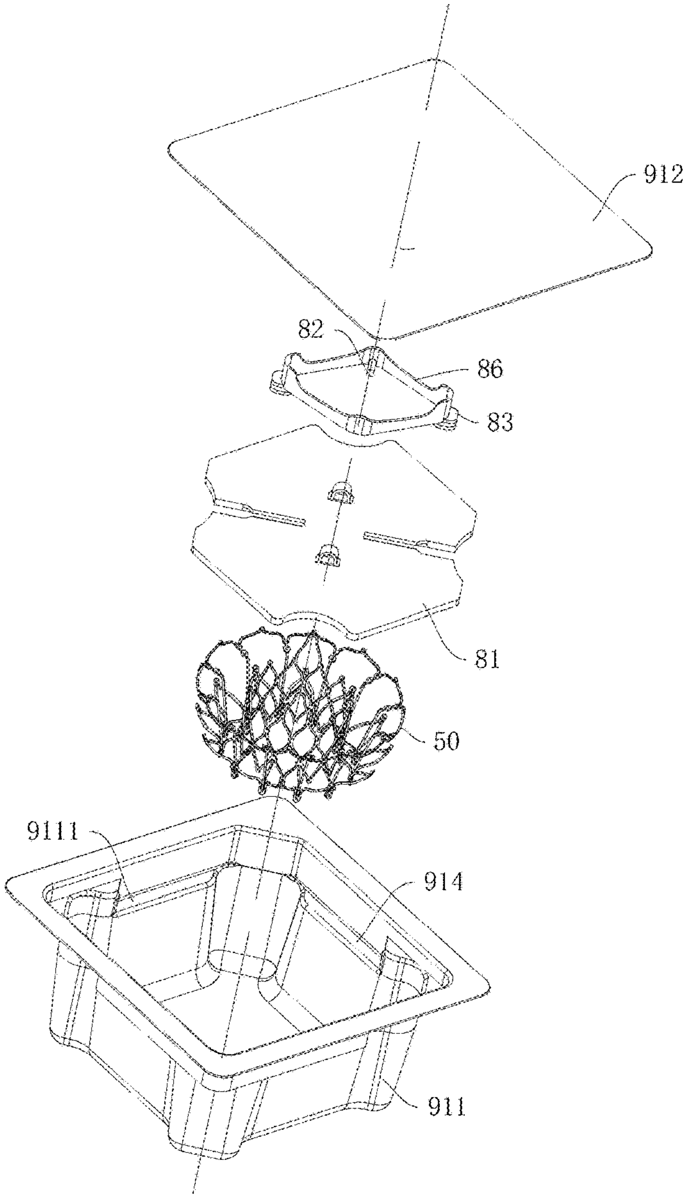
FIG. 29 is an exploded view of the packaging box in FIG. 28.
Figure 30:
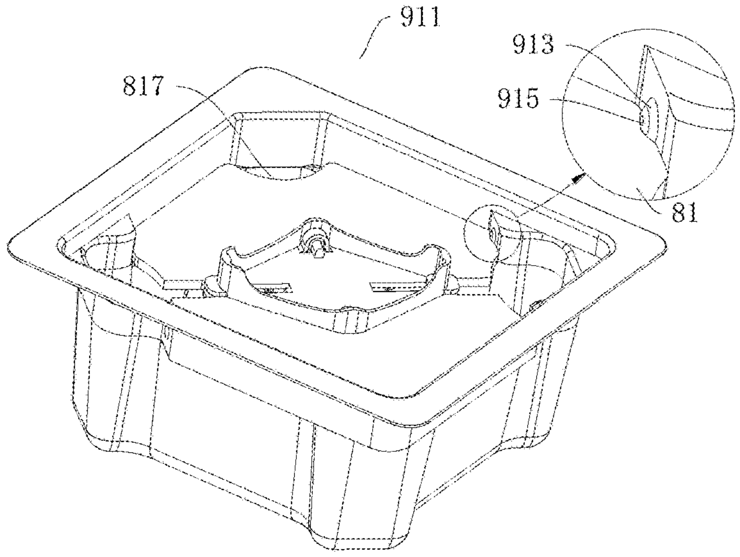
FIG. 30 is a schematic view of the box body and the holder in FIG. 28.
Figure 31:
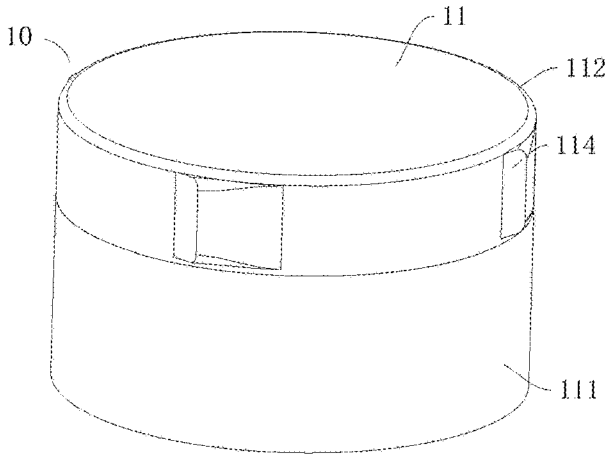
FIG. 31 is a schematic view of a packaging box for a prosthetic valve according to an embodiment of the present disclosure.
Figure 32:
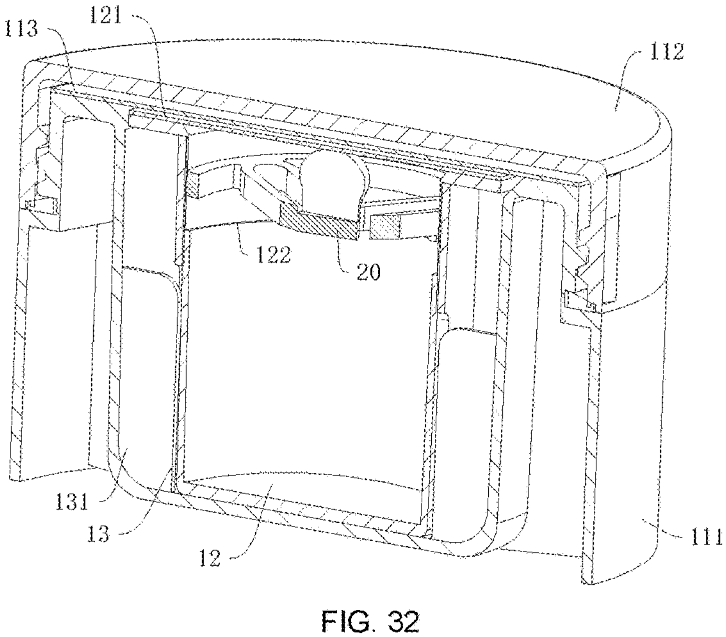
FIG. 32 is a cross-sectional view of the packaging box in FIG. 31.
Figure 33:
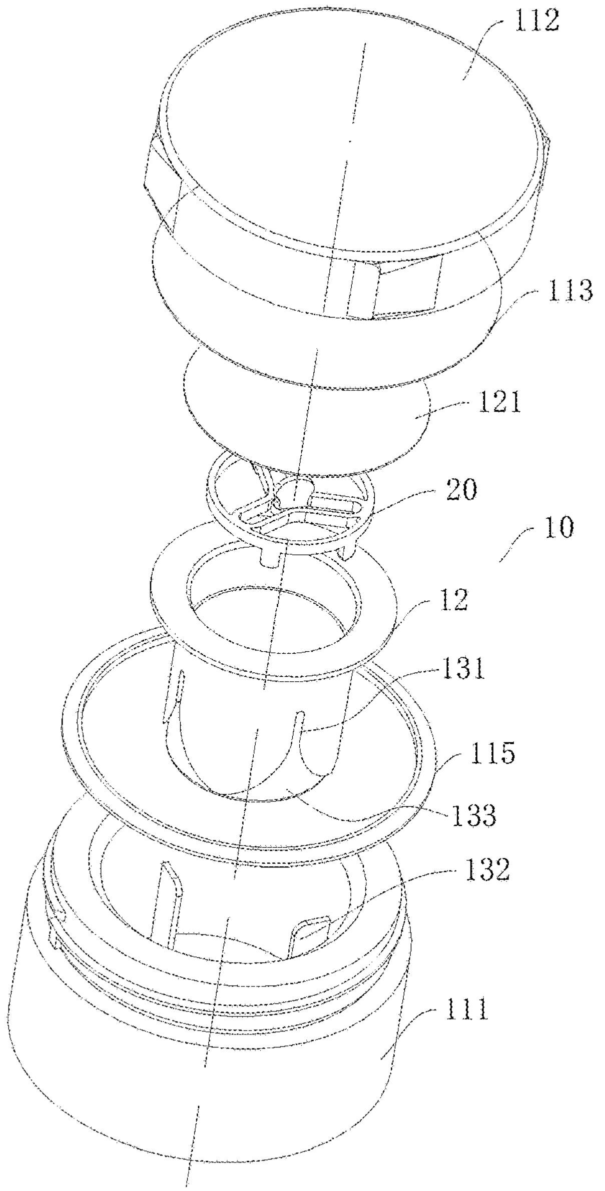
FIG. 33 is an exploded view of the packaging box in FIG. 31.
Figure 34:
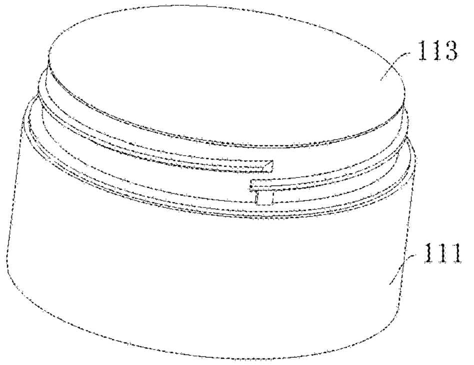
FIG. 34 is a schematic view of the outer box body in FIG. 31.
Figure 35:
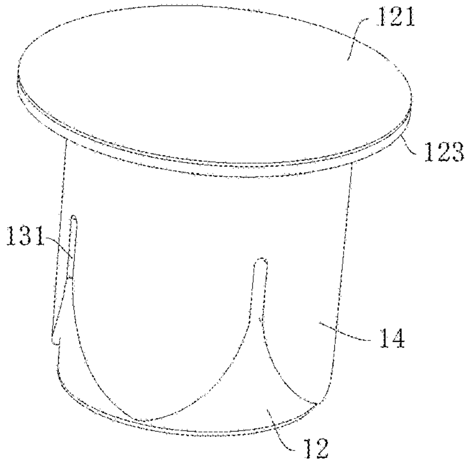
FIG. 35 is a schematic view of the inner container in FIG. 31.
Figure 36:
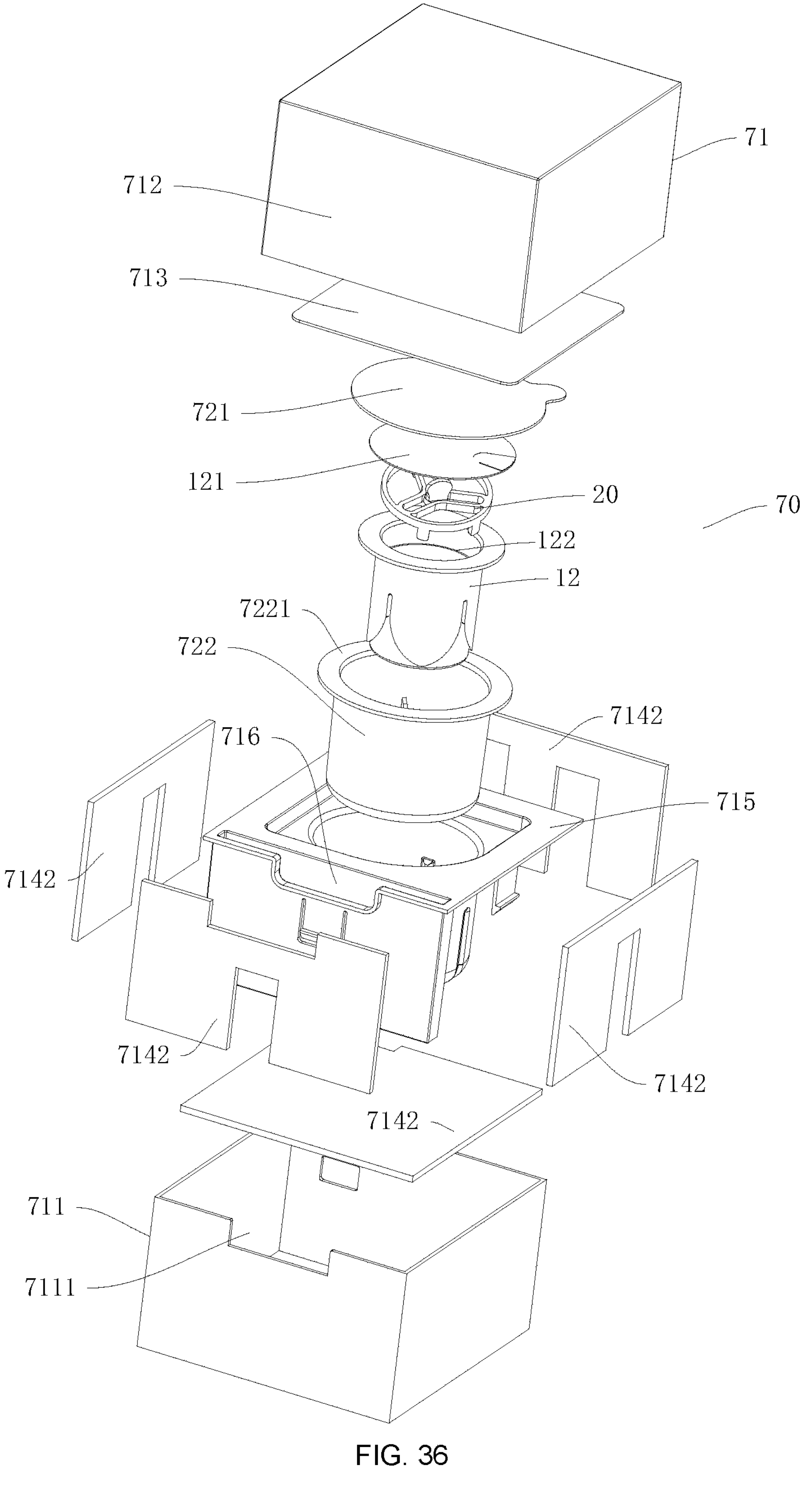
FIG. 36 is an exploded view of a packaging box for a prosthetic valve according to an embodiment of the present disclosure.
Figure 37:
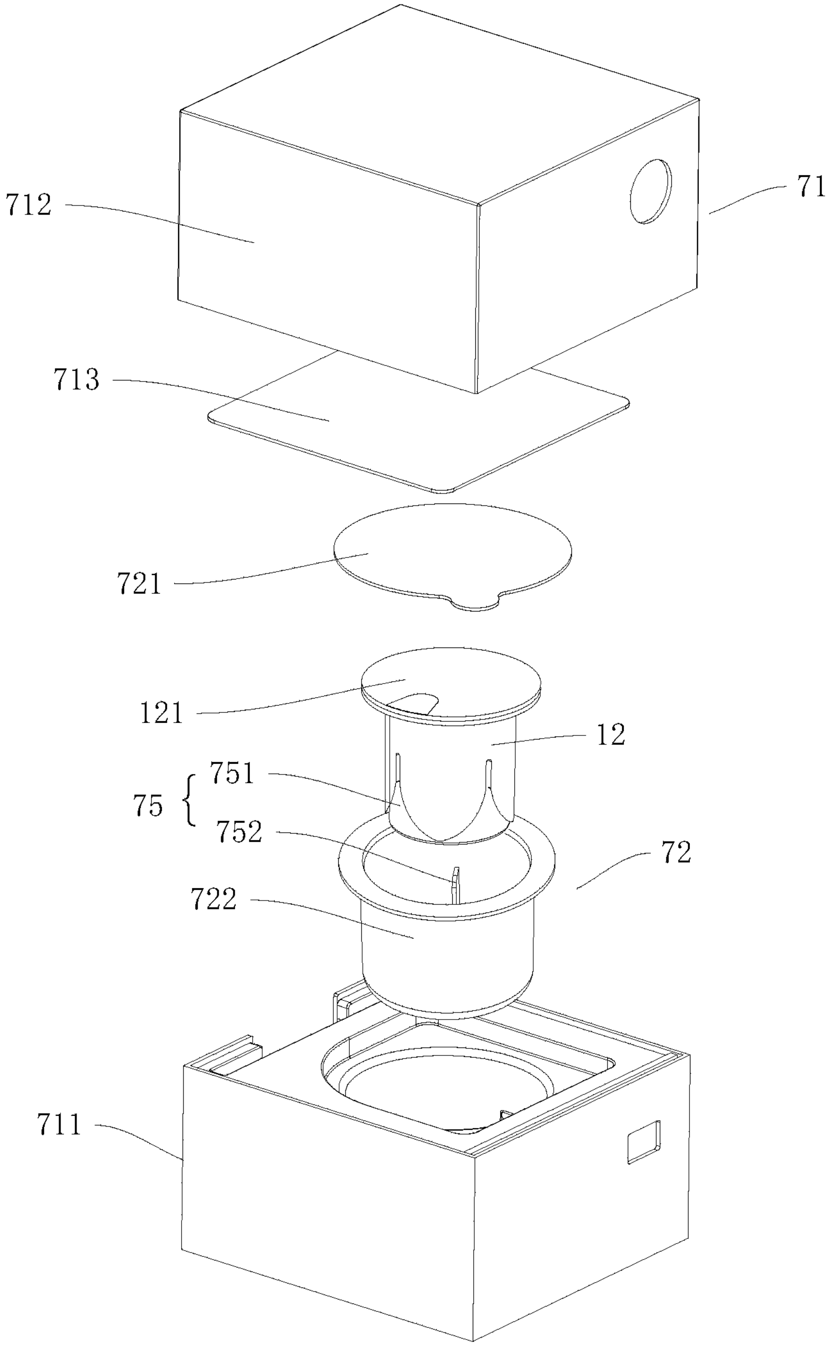
FIG. 37 is an exploded view of the packaging box in FIG. 36 from another perspective.
Figure 38:
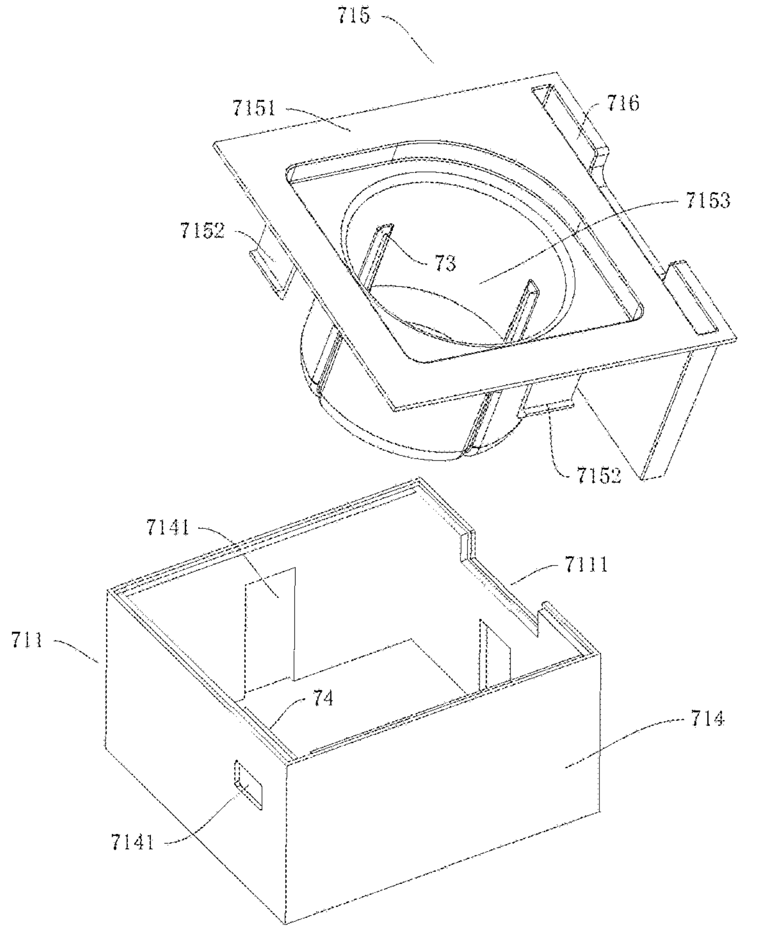
FIG. 38 is a schematic view of the outer box in FIG. 36.
Figure 39:
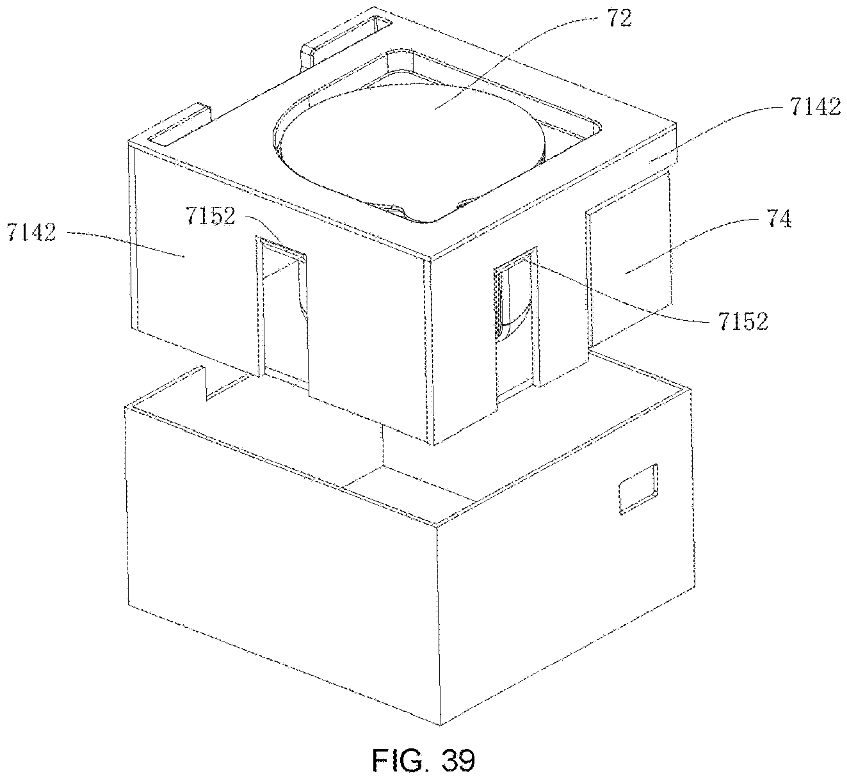
FIG. 39 is a schematic view of the outer box and the middle box in FIG. 36.

Referring to FIGS. 28 to 30, an embodiment of the present disclosure further discloses a packaging box 90 for the prosthetic valve 50, which includes an outer box 91. The outer box 91 includes an outer box body 911 and a box cover 912 that match with each other. The outer box body 911 is provided with a holder 80 according to the above embodiment therein.

The outer box 911 has an open box structure (the cross section of the outer box 911 in the figure is roughly rectangular). The outer peripheral wall of the base 81 and the inner wall of the outer box 911 are in close contact or clearance fit. The outer box body 911 and the box cover 912 are connected by snapping, screwing, gluing or heat fusion. For example, the end of the outer box 911 on the open side is radially enlarged to form an attachment portion, and the box cover 912 and the attachment portion are connected by adhesion, heat fusion, or other means.

In this embodiment, the inner wall of the outer box 911 is provided with a positioning step 914, and the bottom side 812 of the base 81 is placed on the positioning step 914. The positioning step 914 determines the position of the base 81 inside the outer box 911 in the depth direction and prevents the prosthetic valve 50 from contacting the bottom wall of the outer box 911. That is, the prosthetic valve 50 is suspended in the outer box 911.

In the circumferential direction of the base 81, the positioning step 914 can extend continuously or discontinuously. As shown in the figure, the positioning step 914 includes four step units 9111 which are spaced from each other, and each step unit 9111 is located on a corresponding inner wall of the outer box 911. The base 81 is arranged opposite to the bottom wall of the outer box 911.

In this embodiment, the inner wall of the outer box 911 is further provided with an anti-detachment protrusion 915. The anti-detachment protrusion 915 is located on the top side 811 of the base 81 to restrict the edge of the base 81.

At least part of the anti-detachment protrusion 915 abuts against the top side 811 of the base 81, and the abutting part is close to the edge of the base 81, thereby preventing the base 81 from detaching from the outer box body 911. When installing the base 81 in the outer box body 911, the edge of the base 81 can move over the anti-detachment protrusion 915.

The top and bottom of the anti-detachment protrusion 915 are each provided with an inclined guide surface 913, to facilitate the movement of the base 81 over the anti-detachment protrusion 915. For example, the anti-detachment protrusion 915 in the figure is in the shape of a spheroidal.

A plurality of anti-detachment protrusions 915 can be provided, which are arranged in sequence and spaced from each other in the circumferential direction of the base 81. As shown in the figure, there are four anti-detachment protrusions 915, each of which is located above one of the step units 9111.

In this embodiment, at least a portion of the edge of the base 81 is concave, so that a gap is created between the edge of the concave portion 817 and the inner wall of the outer box body 911, which is communicated with the space below the base 81, in order to facilitate the removal and placement of the base 81.

In the figure, there are four concave portions 817 distributed in the circumferential direction of the base 81. In this embodiment, the cross section of the outer box body 911 is in shape of a rectangle, and the concave portions 817 are located at the corners of the rectangle, maximizing the utilization of the space inside the outer box body 911.

Referring to FIGS. 28 to 30, an embodiment of the present disclosure further discloses a packaging system for a prosthetic valve, including a packaging box 90 according to the above embodiment and a prosthetic valve 50 in the outer box body 911 and connected to the holder 80.

At one axial end of the prosthetic valve 50, the vertices of a plurality of meshes (for example, in the figure, two meshes) protrude relative to the vertices of other meshes, and the protruding meshes can extend into the corresponding engagement openings 814. The positions of the engagement openings 814 correspond to the positions of the corresponding protruding meshes, which can facilitate the positioning and prevent the inner walls of the engagement openings 814 from applying force on the prosthetic valve 50 to cause unnecessary deformation of the prosthetic valve 50.

When packaging the prosthetic valve 50, the prosthetic valve 50 is first fixed to the base 81, and then the base 81 carrying the prosthetic valve 50 is placed in the outer box body 911, and finally the outer box body 911 is sealed by the box cover 912.

The packaging system for the prosthetic valve generally has the following benefits: the difficulty of assembling the prosthetic valve 50 with the base 81 can be reduced and the space utilization in the packaging box 90 can be improved.

Referring to FIGS. 31 to 35, an embodiment of the present disclosure further provides a packaging box 10 for a prosthetic valve 50, which includes an inner container 12 and an outer box 11. The inner container 12 is provided with a holder 20 according to the above embodiment.

The inner container 12 is in a cylindrical shape (for example, the cylinder as shown in the figure). One axial end of the inner container 12 is closed and the other end has an opening. The opening is covered with a first sealing film 121. The end of the inner container 12 with the opening is radially enlarged to form an attachment portion 123, and the first sealing film 121 and the attachment portion 123 are connected by adhesion, heat fusion, or other means.

The inner wall of the inner container 12 has a limiting step 122 matching with the holder 20. The limiting step 122 is used to limit the axial position of the holder 20 (for example, the base 21 of the holder 20 or the end of the lock 22 facing the bottom side 216 of the base 21) in the inner container 12. The bottom side of the holder 20 is arranged opposite to the bottom wall of the inner container 12.

The outer peripheral side of the base 21 of the holder 20 and the inner wall of the inner container 12 are in close contact or clearance fit with each other.

When the holder 20 holds the prosthetic valve 50, the limiting step 122 is configured so that a certain gap is created between the bottom of the prosthetic valve 50 and the bottom wall of the inner container 12, that is, the prosthetic valve 50 is suspended in the inner container 12. The outer box 11 includes an outer box body 111 and a box cover 112 that are snapped with each other. The inner container 12 is located in the outer box body 111. There is a gap between the outer wall of the inner container 12 and the inner wall of the outer box body 111, or the outer wall of the inner container 12 and the inner wall of the outer box body 111 are in close contact with each other.

The outer box body 111 is cylindrical (for example, the cylinder as shown in the figure). One axial end of the outer box body 111 is closed and the other end is open with an opening. The opening is covered with a second sealing film 113 by adhesion, heat fusion, or other means. When the inner container 12 is assembled into the outer box body 111, the axial direction of the inner container 12 and the axial direction of the outer box body 111 are parallel to or coincident with each other.

The outer box body 111 and the box covers 112 can be connected by screwing. For example, the outer peripheral wall of the outer box body 111 at the opening has a male thread, and the inner wall of the box cover 112 has a female thread that engages with the male thread. A sealing ring 115 is disposed between the box cover 112 and the outer box body 111.

The box cover 112 is provided with force application portions 114 protruding outwardly on the outer peripheral wall thereof. There force application portions 114 are distributed in the circumferential direction of the box cover 112. The quantity of force application portions 114 can be 2, 3, 4 or more. The quantity of force application portions 114 in the figure is four, and the force application portions are evenly spaced from each other in the circumferential direction of the box cover 112.

In the circumferential direction of the box cover 112, the two side walls of the force-applying portion 114 intersect at the side away from the box cover 112. In the axial direction of the box cover 112, the height of the force-applying portion 114 is substantially equal to the height of the box cover 112.

In this embodiment, a circumferential positioning mechanism 13 is provided between the inner wall of the outer box body 111 and the outer wall of the inner container 12. The circumferential positioning mechanism 13 includes positioning grooves 131 defined on the outer wall of the inner container 12 and positioning ribs 132 provided on the inner wall of the outer box body 111 and matching with the corresponding positioning grooves 131. Alternatively, the positioning groove 131 can be defined on the inner wall of the outer box body 111 and the positioning rib 132 can be provided on the outer wall of the inner container 12.

The quantity of the positioning grooves 131 is equal to the quantity of the positioning ribs 132. In the figure, the quantity of the positioning grooves 131 is four, and the four positioning grooves 131 are evenly spaced from each other in the circumferential direction of the inner container 12.

The bottom side of the positioning groove 131 defines an opening for the positioning rib 132 to enter the positioning groove 131, and the opening has a flared section 133 for guiding the positioning rib 132 to enter the positioning groove 131. The edges of the flared sections 133 of two circumferentially adjacent positioning grooves 131 are connected, so that the positioning rib 132 can be blindly inserted into the corresponding positioning groove 131, which facilitates the installation of the inner container 12.

The radially protruding portion on the outer wall of the inner container 12 relative to the positioning grooves 131 can be a part of the inner container 12 or an additional component. For example, the radially protruding portion on the outer wall of the inner container 12 can be a sleeve 14 fixed to the outer wall of the inner container 12.

Referring to FIGS. 36 to 39, an embodiment of the present disclosure further provides a packaging box 70 for a prosthetic valve 50, including an inner container 12, a middle box 72 and an outer box 71 that are nested in sequence from the inside to the outside. The inner container 12 can be provided with a holder 20 according to the above embodiment.

The inner container 12 is in a cylindrical shape (for example, the cylinder in the figure). One axial end of the inner container 12 is closed and the other end has an opening. The opening is covered with a first sealing film 121. The end of the inner container 12 with the opening and the first sealing film 121 are connected through adhesion, heat sealing, etc., thereby forming a first layer of sterile packaging.

The inner wall of the inner container 12 has a limiting step 122 matching with the holder 20. The limiting step 122 is used to limit the insertion depth of the holder 20 so that a certain gap is formed between the bottom of the prosthetic valve 50 and the bottom wall of the inner container 12, that is, the prosthetic valve 50 is suspended in the inner container 12.

The outer box 71 includes an outer box body 711 and a box cover 712 that are snapped with each other. The outer box body 711 is in the shape of a prism (for example, a quadrangular prism as shown in the figure). One axial end of the outer box body 711 is closed and the other end has an opening, and the opening is covered with a second sealing film 713 through adhesion, heat sealing, etc., thereby forming a protective barrier.

The middle box 72 includes a middle box body 722, and the inner container 12 is located in the middle box body 722. The opening of the middle box body 722 is covered with a third sealing film 721. Therefore, a double-layer sterile packaging is provided.

Regarding the material of the three sealing films, the first sealing film 121 is made of a breathable and waterproof material, such as Tyvek cover material, to achieve single-layer sterile breathable packaging. The third sealing film 721 is made of a breathable and waterproof material, such as Tyvek cover material, to achieve double-layer sterile breathable packaging, which is suitable for EO sterilization. The second sealing film 713 is made of a non-breathable and waterproof material, such as aluminum foil cover material, aluminum-plastic composite panel among other materials, to achieve a moisture protection effect and solve the moisture problem during storage and transportation.

In addition, the first sealing film 121, the third sealing film 721, and the second sealing film 713 are all provided with easy-tearing corners for easy tearing by the user.

A circumferential positioning mechanism 75 is provided between the inner wall of the middle box body 722 and the outer wall of the inner container 12. The circumferential positioning mechanism 75 includes positioning grooves 751 and positioning ribs 752 matching with the positioning grooves 751. For example, the positioning groove 751 is defined on the outer wall of the inner container 12, and the positioning rib 752 is provided on the inner wall of the middle box body 722, or vice versa. When the positioning rib 752 is inserted in the positioning groove 751, the positioning rib 752 and the inner walls of the positioning groove 751 that are opposite to each other in the circumferential direction of the inner container 12 are in contact or clearance fit with each other.

Spacers 73 are provided between the middle box body 722 and the outer box body 711 to create a gap between them. For example, protruding spacers 73 can be provided in the outer box 711 to raise the middle box body 722, thereby creating a gap for the EO sterilization cycle. Further, the opening of the middle box body 722 and the top surface of the outer box body 711 are not on the same plane, thereby preventing the heat-sealing mold from directly affecting the sealing of the opening of the middle box body 722 when the outer box and the second sealing film are heat-sealed.

The gap between them includes a radial gap and/or a bottom gap. For example, since there is a gap between the radial and/or bottom walls of the middle box body 722 and the outer box 71 for the EO sterilization cycle, the spacers 73 can be distributed in the radial gap between the middle box body 722 and the outer box body 711, or in the bottom gap between the middle box body 722 and the outer box body 711, thereby supporting the middle box body 722 and preventing the middle box body from shaking.

The inner wall of the outer box body 711 itself is provided with protruding ribs as the spacers 73, and the ribs abut against the circumference of the middle box body 722.

The outer box body 711 has a double-layer structure, including an outer layer 714 and an inner layer 715. The inner wall of the outer layer 714 is provided with slots 7141. The top of the inner layer 715 has an opening, and the opening is provided with a top plate 7151 extending outwardly. The second sealing film 713 is attached and fixed to the top plate 7151 at the edge of the flat top plate 7151, thereby enhancing the heat-sealing effect of the second sealing film. The edge of the top plate 7151 is provided with snaps 7152, and the snaps 7152 engage with the slots 7141, thereby fixedly snapping the outer layer 714 with the inner layer 715. Compared with a sing-piece structure, the double-layer structure can simplify the manufacture of the outer box body 711 and reduce the manufacturing cost.

A temperature sensor 74 is provided inside the double-layer structure. A temperature display screen is embedded in the side wall of the outer layer 714. The temperature display screen receives signals from the temperature sensor 74 and displays the temperature accordingly, thereby providing the operator with a temperature indication window.

The outer layer 714 is fitted with lining plates 7142, and the slots 7141 are opened on the lining plates 7142 on the corresponding sides. As shown in the figure, the four sides and bottom surface of the outer layer 714 are all fixed with lining plates 7142.

The top plate 7151 extends toward the interior of the double-layer on one side to form a storage bin 716 with an opening at the top, and the storage bin 716 is used to place the instruction manual. The outer wall of the storage bin 716 and the corresponding portion of the outer side define an access opening 7111 communicated to the opening of the storage bin, so that the operator can conveniently take the instruction manual.

The middle of the top plate 7151 has a sunken area 7153, the inner layer 715 is cylindrical and the opening is located in the sunken area 7153, in order to adapt to the shape of the inner container 12 and the middle box body 722, and reduce the radial and bottom gaps between the components after assembly.

The opening of the middle box body 722 has an outer flange 7221, and the outer flange 7221 is overlapped on the top surface of the sunken area 7153 to increase the contacting area between the middle box body 722 and the inner layer 715, so that the middle box body 722 is stably installed in the inner layer 715.

The packaging box 70 according to this embodiment has a double-layer sterile and breathable structure formed by the inner container and the middle box, in order to ensure that the implant is always in a sterile and safe environment. Further, the waterproof and breathable second sealing film 713 provides a protective barrier, ensuring that the dry valve is isolated from moisture in the external environment during storage and transportation, achieving a moisture protection effect.

In addition, the packaging box 70 is compact as a whole, which reduces the difficulty of transportation. The unpacking operation is simple. Only the box cover needs to be removed and the three layers of sealing film need to be torn off layer by layer, then the holder 20 can be taken out. This also avoids the operational difficulties and complexities caused by repeated unpacking, thereby improving the convenience of unpacking operation in the preoperative preparation before implantation.

Figure 40:
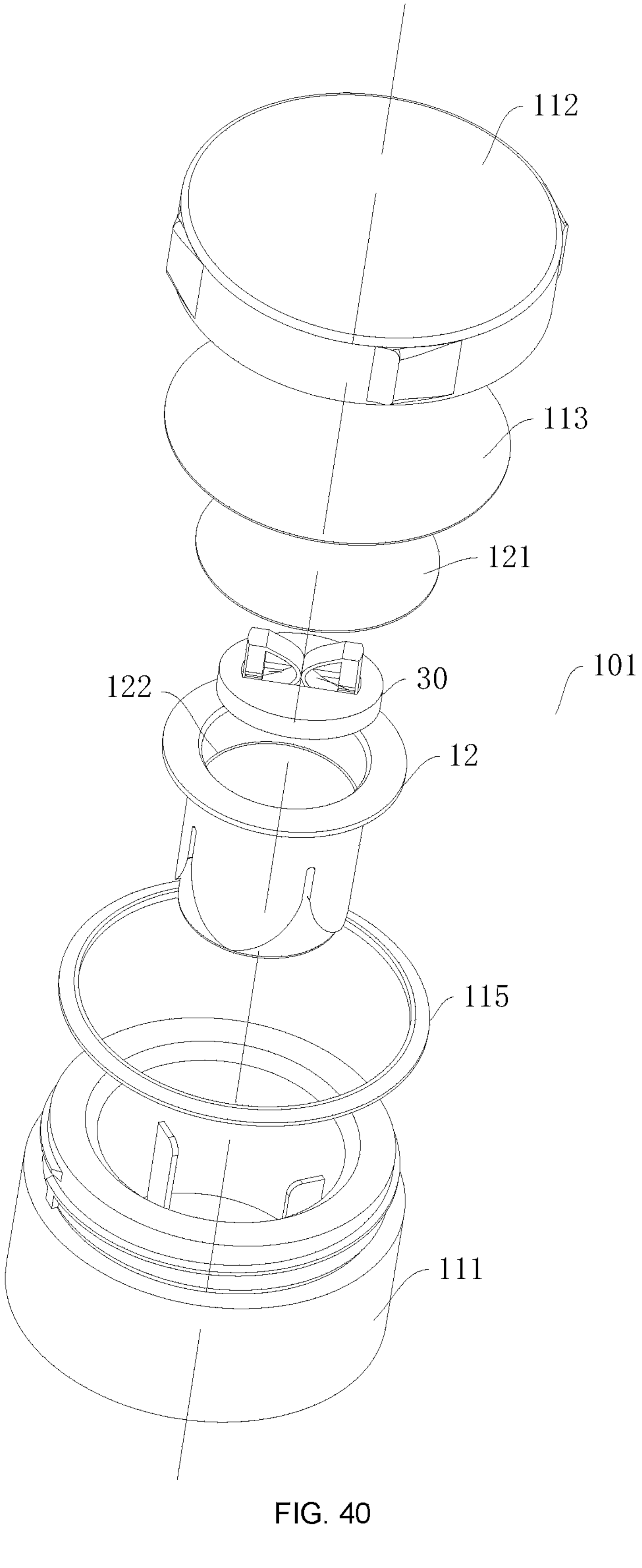
FIG. 40 is an exploded view of a packaging box for a prosthetic valve according to an embodiment of the present disclosure.

Referring to FIG. 40, an embodiment of the present disclosure further discloses a packaging box 101 for a prosthetic valve 50. The structure of the packaging box 101 is the same as that of the packaging box 10 according to the above embodiment, and the only difference is that the holder is the holder 30 according to the above embodiment.

Figure 41:
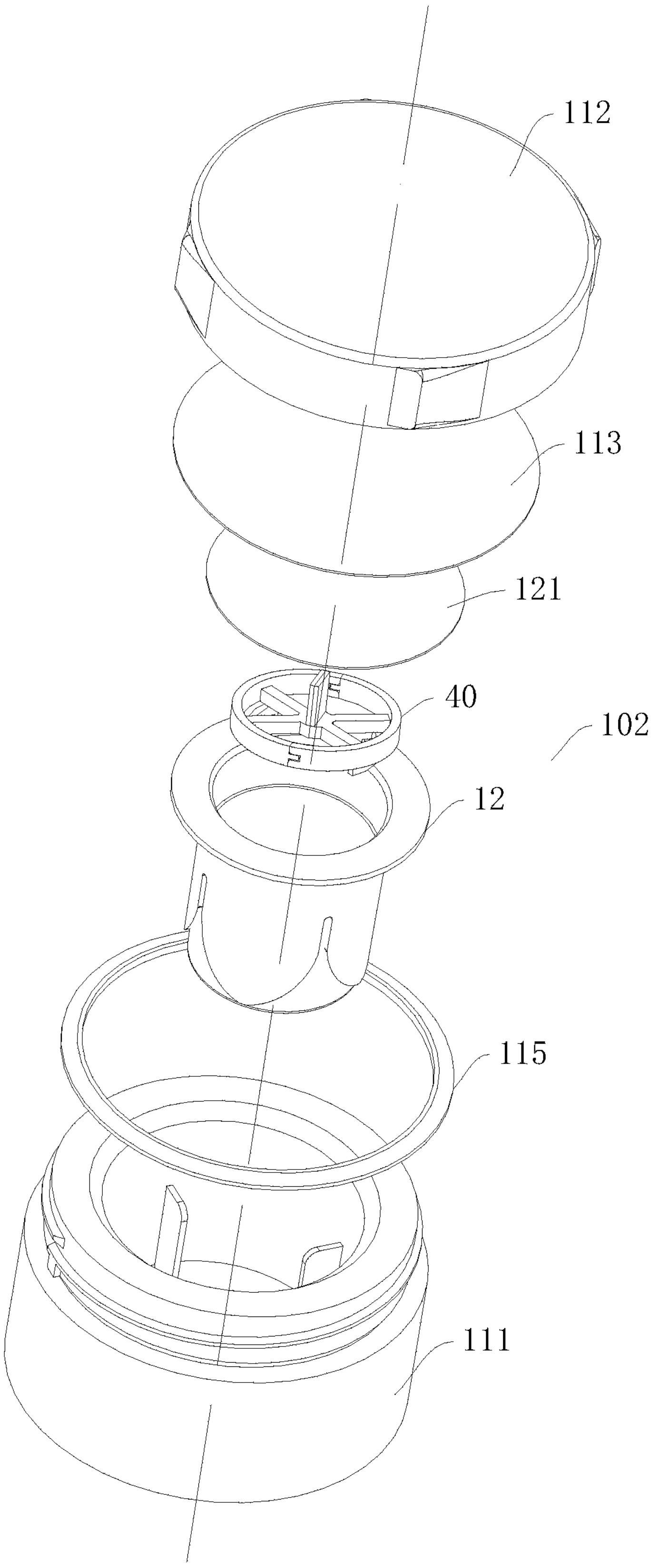
FIG. 41 is an exploded view of a packaging box for a prosthetic valve according to an embodiment of the present disclosure.

Referring to FIG. 41, an embodiment of the present disclosure further discloses a packaging box 102 for a prosthetic valve 50. The structure of the packaging box 102 is the same as that of the packaging box 10 according to the above embodiment, and the only difference is that the holder is the holder 40 according to the above embodiment.

Figure 42:
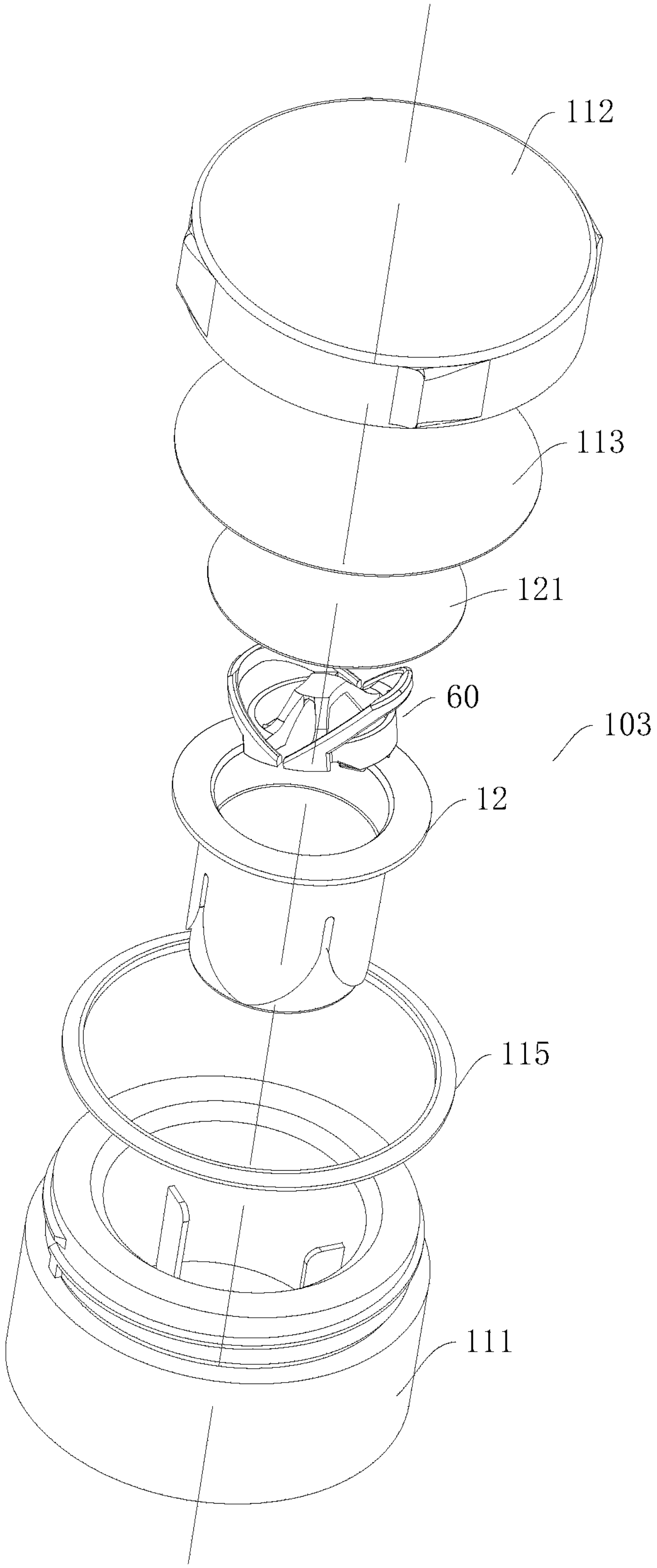
FIG. 42 is an exploded view of a packaging box for a prosthetic valve according to an embodiment of the present disclosure.

Referring to FIG. 42, an embodiment of the present disclosure further provides a packaging box 103 for a prosthetic valve 50. The structure of the packaging box 103 is the same as that of the packaging box 10 according to the above embodiment, and the only difference is that the holder is the holder 60 according to the above embodiment.

Figure 43:
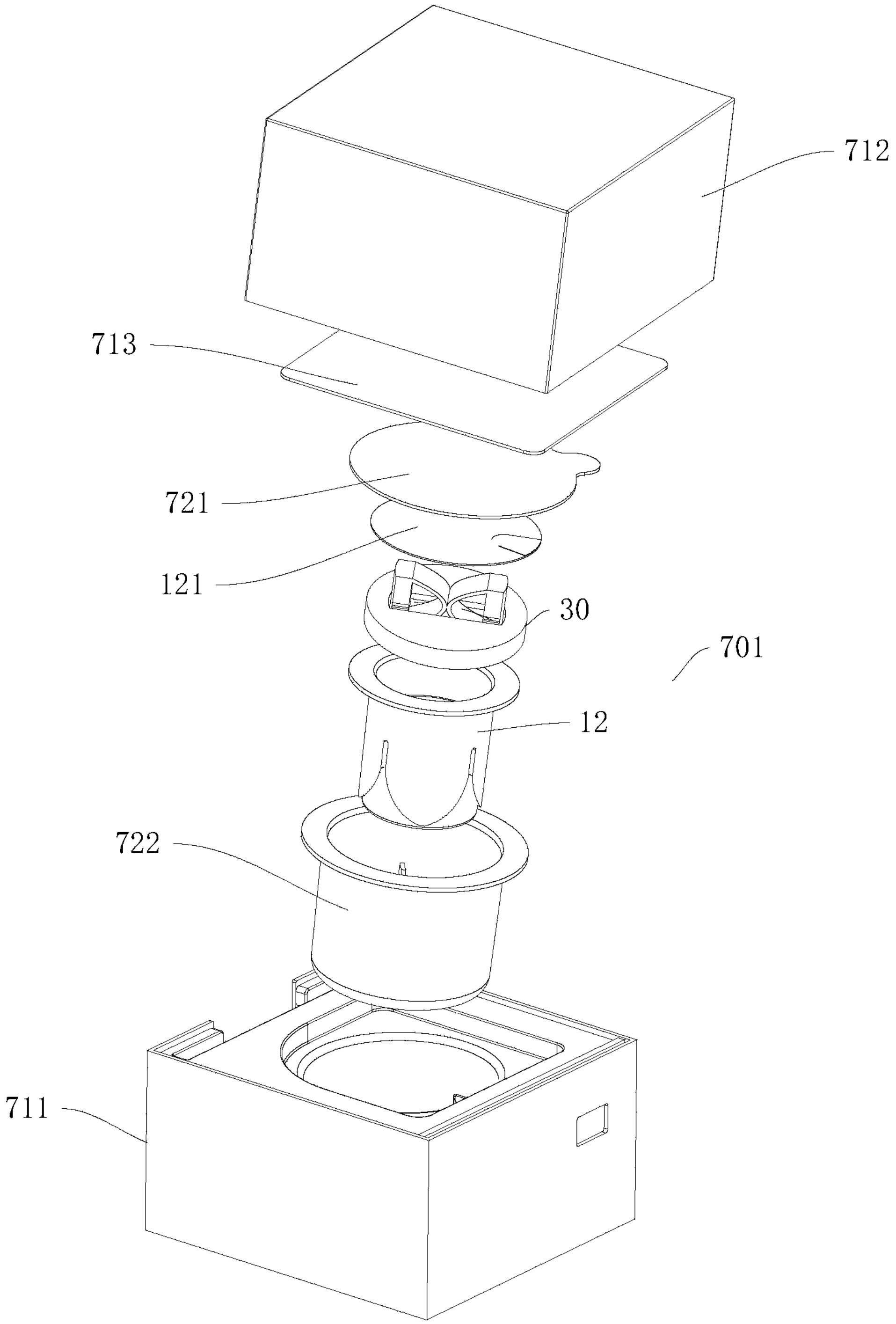
FIG. 43 is an exploded view of a packaging box for a prosthetic valve according to an embodiment of the present disclosure.

Referring to FIG. 43, an embodiment of the present disclosure further discloses a packaging box 701 for a prosthetic valve 50. The structure of the packaging box 701 is the same as that of the packaging box 70 according to the above embodiment, and the only difference is that the holder is the holder 30 according to the above embodiment.

Figure 44:
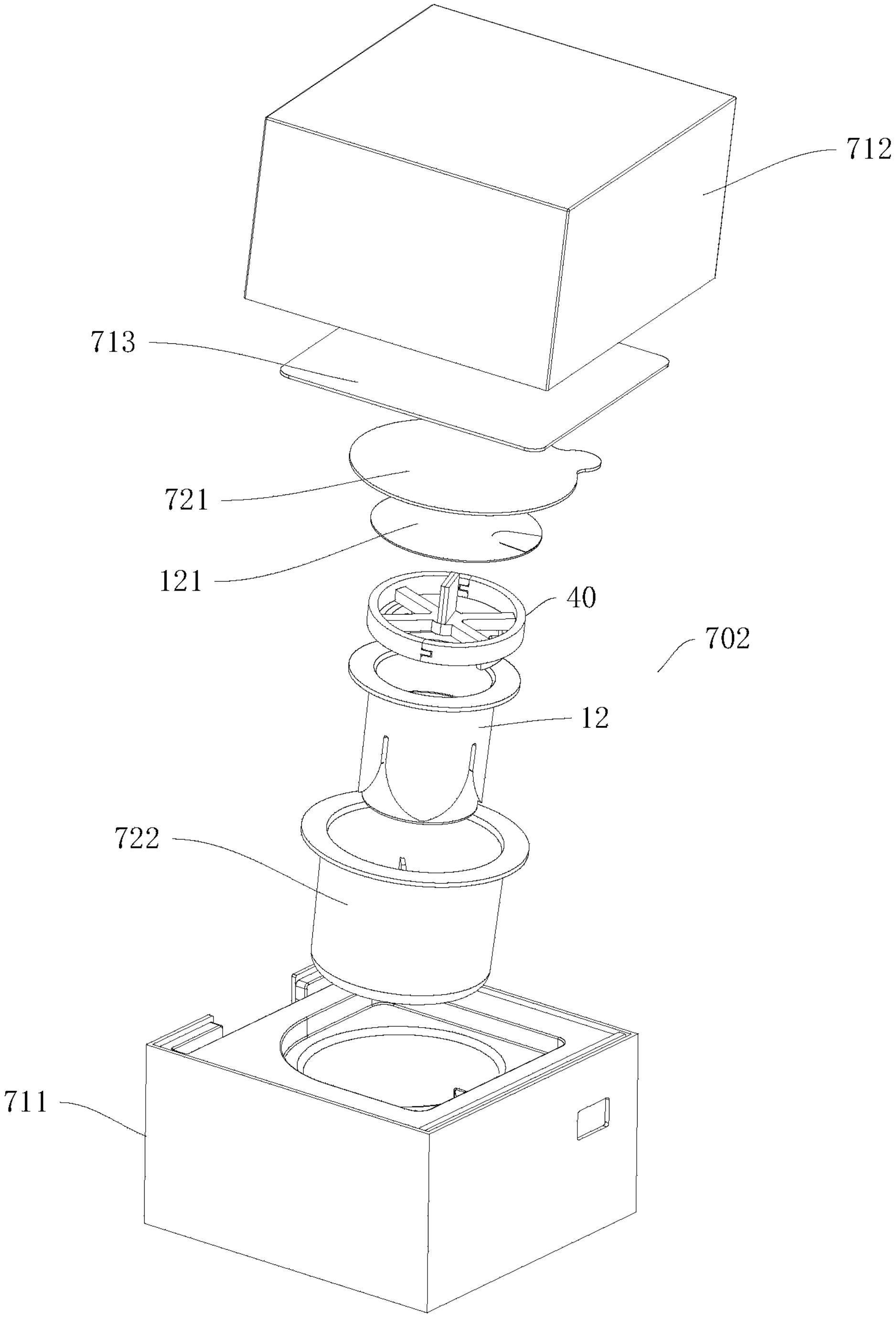
FIG. 44 is an exploded view of a packaging box for a prosthetic valve according to an embodiment of the present disclosure.

Referring to FIG. 44, an embodiment of the present disclosure further provides a packaging box 702 for a prosthetic valve 50. The structure of the packaging box 702 is the same as that of the packaging box 70 according to the above embodiment, and the only difference is that the holder is the holder 40 according to the above embodiment.

Figure 45:
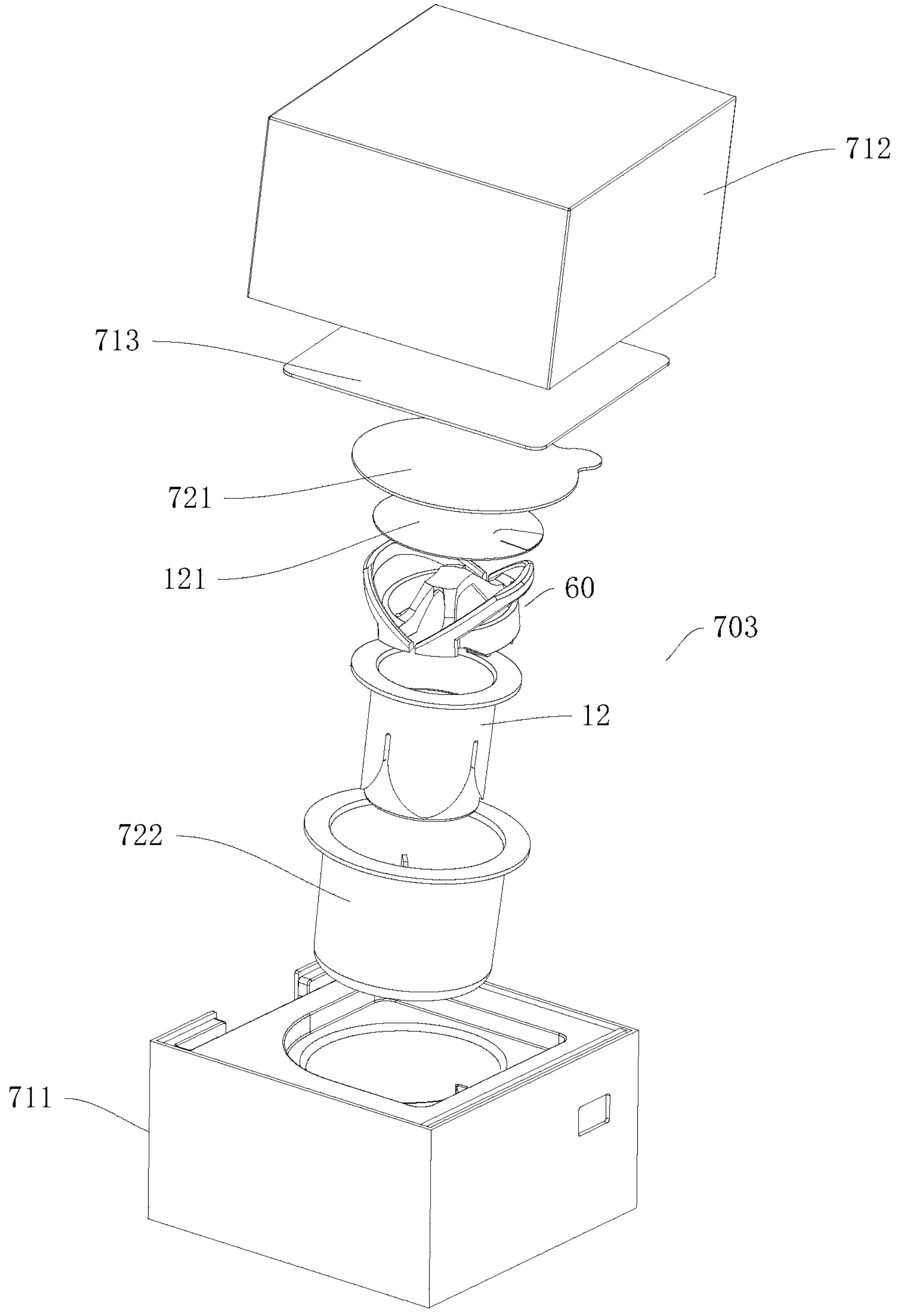
FIG. 45 is an exploded view of a packaging box for a prosthetic valve according to an embodiment of the present disclosure.

Referring to FIGS. 45, an embodiment of the present disclosure further provides a packaging box 703 for a prosthetic valve 50. The structure of the packaging box 703 is the same as that of the packaging box 70 according to the above embodiment, and the only difference is that the holder is the holder 60 according to the above embodiment.

For the packaging boxes according to the above embodiments, in the case where a multi-layer structure with an inner layer and an outer layer in a nested configuration is used, the outermost layer (i.e., the outer box) can be in the shape of a soft bag (i.e., a packaging bag that provides a sealed environment).

With reference to FIGS. 28 to 30, an embodiment of the present disclosure further discloses a packaging system for a prosthetic valve, including a packaging box 90 according to the above embodiment and a prosthetic valve in an outer box body 911 and connected to a holder 80.

Some embodiments of the present disclosure further provide various packaging systems for prosthetic valve, including the packaging box 10 or the packaging box 70 according to the embodiments as shown in FIGS. 31 to 45. Each packaging box has an inner container 12, and a holder and a prosthetic valve are disposed in the inner container 12.

In the radial direction of the prosthetic valve, the claws 22 are located on the outside or inside of the prosthetic valve in a transition fit with the prosthetic valve in the radial direction. That is, the radial pre-stress of the claws 22 on the prosthetic valve is very small and will not cause excessive deformation of the prosthetic valve.

In the case where the hold is the holder 20 according to the above embodiment, in the radial direction of the prosthetic valve 50, the connecting arms 222 of the claws 22 are located outside the prosthetic valve.

In the case where the hold is the holder 30 according to the above embodiment, in the radial direction of the prosthetic valve 50, the connecting arms 321 of the claws 32 are located inside the prosthetic valve.

In the case where the hold is the holder 40 according to the above embodiment, in the radial direction of the prosthetic valve 50, the arc-shaped ribs 422 of the claws 42 are located outside the prosthetic valve.

In the case where the hold is the holder 60 according to the above embodiment, in the radial direction of the prosthetic valve 50, the connecting arms 621 of the locks 62 are located outside the prosthetic valve.

An embodiment of the present disclosure further provides a packaging system for a prosthetic valve, including:

a packaging box including an outer box, a middle box and an inner container arranged in sequence from the outside to the inside;

a holder which is located in the inner container and has locks; and a prosthetic valve which is located in the inner container and generally has a cylindrical structure as a whole and hollow structural gaps on the side wall thereof, wherein the locks extend into the corresponding structural gaps.

In this embodiment, the packaging box can use the packaging box 70 according to any of the embodiments as shown in FIGS. 36 to 45, and the holder can use the holder according to any of the above embodiments. The prosthetic valves according to the above embodiments can all use dry film (also called dry valve, which does not need to be soaked in solution and is more convenient for storage and transportation).

The technical features of the above embodiments can be arbitrarily combined, and not all possible combinations of the technical features of the above embodiments have been described for the sake of brevity of description. However, as long as there is no contradiction in the combination of these technical characteristics, such combination should be regarded as falling into the scope of this specification. When the technical features in different embodiments are shown in the same drawing, it can be considered that the drawing also discloses a combined embodiment of various embodiments involved.

The above-described embodiments only illustrate several embodiments of the present disclosure, and the description thereof is specific and detail, but should not be construed as limiting the scope of the patent disclosure. It should be noted that, for those of ordinary skill in the art, several modifications and improvements can be made without departing from the concept of the present disclosure, all of which fall into the protection scope of the present disclosure.

The invention claimed is:

1. A holder for a prosthetic valve, comprising:

a base having a bottom side and a top side opposite to each other, wherein a prosthetic valve assembly area is defined on the bottom side;

a plurality of locks connected to the base, wherein the locks are distributed around the prosthetic valve assembly area, and the locks are configured to engage with the prosthetic valve; and a driving part linked with the locks and having a first position and a relative second position relative to the base, wherein in the first position, the locks hold the prosthetic valve in the prosthetic valve assembly area, and in the second position, the locks are disengaged from the prosthetic valve and allow the prosthetic valve to move out of the prosthetic valve assembly area;

wherein the driving part is fixedly connected to the base, and is configured to switch between the first position and the second position by deformation of the driving part itself and/or the base.

2. The holder for a prosthetic valve of claim 1, wherein the holder for the prosthetic valve further comprises a holding handle, and the holding handle is connected to the base and is located on the top side of the base.

3. The holder for a prosthetic valve of claim 2, wherein the driving part also serves as the holding handle, or the driving part and the holding handle are separately configured and connected to the base respectively.

4. The holder for a prosthetic valve of claim 1, wherein the locks are claws, at least a part of the base is a connecting portion, at least one of the claws is a movable claw connected to a bottom side of the connecting portion, the driving part is a driving handle provided on a top side of the connecting portion, and the driving handle is linked with the movable claw through the connecting portion.

5. The holder for a prosthetic valve of claim 4, wherein a portion of the base adjacent to the connecting portion is a deformable portion, and the deformable portion is made of a resilient material;

the movable claw has an initial state in which the prosthetic valve is gripped and a relative unlocked state in which the prosthetic valve is released; and the driving handle is linked with and configured to drive the movable claw to move toward the unlocked state, and the movable claw is configured to reset to the initial state through the deformable portion.

6. The holder for a prosthetic valve of claim 4, wherein the base has a frame structure, comprising:

an outer ring, wherein the claws are arranged at intervals on the outer ring; and transition arms extending from an inner edge to a central area of the outer ring and connected to the driving part.

7. The holder for a prosthetic valve of claim 6, wherein a section of the outer ring is axially narrowed or radially narrowed to form a deformable portion.

8. The holder for a prosthetic valve of claim 1, wherein the base has a frame structure and comprises:

a middle part;

transition arms, which extend from the middle part outwardly in a radial pattern; and connecting portions located at ends of the transition arms extending outwardly in the radial pattern, wherein the driving part and the locks are all connected to the connecting portions, and the driving part is configured to drive the locks to change the engagement with the prosthetic valve at different positions.

9. The holder for a prosthetic valve of claim 4, wherein relative to the connecting portion, the driving handle is located on the top side of the base, and the locks are located on the bottom side of the base.

10. The holder for a prosthetic valve of claim 1, wherein the the locks extend into structural gaps of the prosthetic valve when engaging with the prosthetic valve.

11. The holder for a prosthetic valve of claim 2, wherein the locks grip connecting ears of the prosthetic valve when engaging with the prosthetic valve.

12. A packaging system for a prosthetic valve, comprising:

a packaging box comprising an outer box, a middle box and an inner container arranged in sequence from outside to inside;

a holder according to claim 1, the holder being located in the inner container and provided with locks;

a prosthetic valve located in the inner container, wherein the prosthetic valve is cylindrical and has hollow structural gaps on a side wall thereof, wherein the locks extend into corresponding structural gaps.

13. A holder for a prosthetic valve, comprising:

a base having a bottom side and a top side opposite to each other, wherein a prosthetic valve assembly area is defined on the bottom side;

a plurality of locks connected to the base, wherein the locks are distributed around the prosthetic valve assembly area, and the locks are configured to engage with the prosthetic valve; and a driving part linked with the locks and having a first position and a relative second position relative to the base, wherein in the first position, the locks hold the prosthetic valve in the prosthetic valve assembly area, and in the second position, the locks are disengaged from the prosthetic valve and allow the prosthetic valve to move out of the prosthetic valve assembly area;

wherein the locks are claws, at least a part of the base is a connecting portion, at least one of the claws is a movable claw connected to a bottom side of the connecting portion, the driving part is a driving handle provided on a top side of the connecting portion, and the driving handle is linked with the movable claw through the connecting portion; and wherein the base has a radial direction in space, and each claw comprises a connecting arm fixed to the base and a claw head located on the connecting arm and protruding in the radial direction, wherein the claw head is configured to engage with the prosthetic valve.

14. A holder for a prosthetic valve, comprising:

a base having a bottom side and a top side opposite to each other, wherein a prosthetic valve assembly area is defined on the bottom side;

a plurality of locks connected to the base, wherein the locks are distributed around the prosthetic valve assembly area, and the locks are configured to engage with the prosthetic valve; and a driving part linked with the locks and having a first position and a relative second position relative to the base, wherein in the first position, the locks hold the prosthetic valve in the prosthetic valve assembly area, and in the second position, the locks are disengaged from the prosthetic valve and allow the prosthetic valve to move out of the prosthetic valve assembly area;

wherein the base has a frame structure and comprises:

a middle part;

transition arms, which extend from the middle part outwardly in a radial pattern; and connecting portions located at ends of the transition arms extending outwardly in the radial pattern, wherein the driving part and the locks are all connected to the connecting portions, and the driving part is configured to drive the locks to change the engagement with the prosthetic valve at different positions; and wherein the transition arms are divided into a plurality of groups, the driving part comprises a plurality of driving handles which are connected to the corresponding transition arms in the corresponding groups.

* * * * *